(12) United States Patent
Connolly et al.

(10) Patent No.: US 11,513,115 B2
(45) Date of Patent: Nov. 29, 2022

(54) METHODS AND APPARATUS FOR MAGNETIC MULTI-BEAD ASSAYS

(71) Applicant: Quantum Diamond Technologies Inc., Somerville, MA (US)

(72) Inventors: Colin B. Connolly, Cambridge, MA (US); Jeffrey D. Randall, Somerville, MA (US); John C. Pena, Cambridge, MA (US)

(73) Assignee: Quantum Diamond Technologies Inc., Somerville, MA (US)

( * ) Notice: Subject to any disclaimer, the term of this patent is extended or adjusted under 35 U.S.C. 154(b) by 526 days.

(21) Appl. No.: 16/467,474

(22) PCT Filed: Dec. 22, 2017

(86) PCT No.: PCT/US2017/068126
§ 371 (c)(1),
(2) Date: Jun. 6, 2019

(87) PCT Pub. No.: WO2018/119367
PCT Pub. Date: Jun. 28, 2018

(65) Prior Publication Data
US 2019/0331674 A1 Oct. 31, 2019

Related U.S. Application Data

(60) Provisional application No. 62/438,593, filed on Dec. 23, 2016.

(51) Int. Cl.
*G01N 33/543* (2006.01)
*G01N 24/10* (2006.01)
(Continued)

(52) U.S. Cl.
CPC ....... *G01N 33/54326* (2013.01); *G01N 24/10* (2013.01); *G01N 27/745* (2013.01);
(Continued)

(58) Field of Classification Search
None
See application file for complete search history.

(56) References Cited

U.S. PATENT DOCUMENTS 4,279,617 A 7/1981 Masson et al.
4,628,037 A 12/1986 Chagnon et al.
(Continued)

FOREIGN PATENT DOCUMENTS

EP 0430371 A2 6/1991
JP 2010/506191 A 2/2010
(Continued)

OTHER PUBLICATIONS https://crisp.nus.edu.sg/~research/tutorial/tmp/image.htm (Year: 2001).*
(Continued)

*Primary Examiner* — Rebecca M Giere
*Assistant Examiner* — Xiaoyan Zou
(74) *Attorney, Agent, or Firm* — Foley Hoag LLP; Rajesh Vallabh

(57) ABSTRACT

The present application discloses methods and apparatus for detecting a complex including an analyte that include contacting a sample in a solution with a population of functionalized beads of a first type, which are magnetic functionalized beads and are functionalized to include a first moiety that associates with an analyte under suitable conditions, contacting the sample solution with a population of functionalized beads of a second type, which are functionalized to include a second moiety that associates with the analyte under suitable conditions, contact resulting in formation of a complex including one of the first type of functionalized bead, the analyte, and one of the second type of functionalized bead, and detecting the complex including the analyte by detecting magnetic fields produced by the magnetic functionalized bead and by detecting the functionalized bead of the second type associated with the analyte in the complex.

17 Claims, 15 Drawing Sheets

(51) Int. Cl.
*G01N 33/536* (2006.01)
*G01N 27/74* (2006.01)
*G01N 33/553* (2006.01)
*G01R 33/26* (2006.01)
*G01R 33/32* (2006.01)

(52) U.S. Cl.
CPC ......... *G01N 33/536* (2013.01); *G01N 33/553* (2013.01); *G01R 33/26* (2013.01); *G01R 33/323* (2013.01)

(56) References Cited

U.S. PATENT DOCUMENTS

| | | |
|---|---|---|
| 4,695,392 A | 9/1987 | Whitehead et al. |
| 5,145,784 A | 9/1992 | Cox et al. |
| 5,547,555 A | 8/1996 | Schwartz et al. |
| 5,648,124 A | 7/1997 | Sutor |
| 5,998,224 A | 12/1999 | Rohr et al. |
| 6,050,138 A | 4/2000 | Lynch et al. |
| 6,097,790 A | 8/2000 | Hasegawa et al. |
| 6,178,033 B1 | 1/2001 | Ford et al. |
| 6,231,643 B1 | 5/2001 | Pasic et al. |
| 6,602,714 B1 | 8/2003 | Tagge et al. |
| 6,896,850 B2 | 5/2005 | Subramanian et al. |
| 7,086,288 B2 | 8/2006 | Lee et al. |
| 7,279,286 B2 | 10/2007 | Kannt et al. |
| 7,474,180 B2 | 1/2009 | Bintoro et al. |
| 7,489,593 B2 | 2/2009 | Nguyen-Dinh et al. |
| 7,635,571 B2 | 12/2009 | Ullman et al. |
| 7,863,035 B2 | 1/2011 | Clemens et al. |
| 8,142,892 B2 | 3/2012 | Rida |
| 8,193,808 B2 | 6/2012 | Fu et al. |
| 8,236,574 B2 | 8/2012 | Duffy et al. |
| 8,520,211 B2 | 8/2013 | Schleipen et al. |
| 8,670,524 B2 | 3/2014 | Mann et al. |
| 8,691,557 B2 | 4/2014 | Sooryakumar et al. |
| 8,697,435 B2 | 4/2014 | Heil et al. |
| 8,846,415 B2 | 9/2014 | Duffy et al. |
| 8,989,354 B2 | 3/2015 | Davis et al. |
| 9,435,791 B2 | 9/2016 | Acosta et al. |
| 9,766,181 B2 | 9/2017 | Englund et al. |
| 9,797,817 B2 | 10/2017 | McNaughton et al. |
| 9,919,313 B2 | 3/2018 | Lowe et al. |
| 10,376,881 B2 | 8/2019 | Lowe et al. |
| 10,845,449 B2 | 11/2020 | Connolly et al. |
| 11,143,594 B2 | 10/2021 | Connolly et al. |
| 2002/0025576 A1 | 2/2002 | Northrup et al. |
| 2005/0053525 A1 | 3/2005 | Segal et al. |
| 2006/0252031 A1 | 11/2006 | Abbott et al. |
| 2007/0012094 A1 | 1/2007 | Degertekin et al. |
| 2007/0103697 A1 | 5/2007 | Degertekin |
| 2007/0155024 A1* | 7/2007 | Miethe ............... G01N 27/745 436/524 |
| 2008/0014442 A1 | 1/2008 | Rida |
| 2008/0108122 A1 | 5/2008 | Paul et al. |
| 2008/0191688 A1 | 8/2008 | Kahlman et al. |
| 2009/0134481 A1 | 5/2009 | Sengupta |
| 2009/0165876 A1 | 7/2009 | Atkin et al. |
| 2010/0193398 A1 | 8/2010 | Marsh et al. |
| 2011/0062957 A1* | 3/2011 | Fu .................... G01N 24/088 324/307 |
| 2011/0065209 A1 | 3/2011 | Heil et al. |
| 2011/0124985 A1 | 5/2011 | Meurville et al. |
| 2011/0170108 A1 | 7/2011 | Degertekin |
| 2012/0115214 A1 | 5/2012 | Battrell et al. |
| 2012/0170134 A1 | 7/2012 | Bolis et al. |
| 2012/0182548 A1 | 7/2012 | Harb et al. |
| 2012/0301893 A1 | 11/2012 | Siciliano et al. |
| 2013/0122485 A1 | 5/2013 | Hong |
| 2013/0122517 A1 | 5/2013 | Henzler et al. |
| 2014/0077231 A1* | 3/2014 | Twitchen ............ G01N 24/10 257/77 |
| 2014/0170639 A1* | 6/2014 | Norvell ............... G01N 33/558 435/5 |
| 2015/0184235 A1 | 7/2015 | Reda et al. |
| 2015/0374250 A1 | 12/2015 | Hatano et al. |
| 2016/0161429 A1* | 6/2016 | Englund ............ G01N 21/6402 324/304 |
| 2016/0282427 A1 | 9/2016 | Heidmann |
| 2016/0356863 A1 | 12/2016 | Boesch et al. |
| 2017/0234941 A1 | 8/2017 | Hatano et al. |
| 2017/0316487 A1 | 11/2017 | Mazed |
| 2018/0246143 A1 | 8/2018 | Grinolds et al. |
| 2019/0331674 A1 | 10/2019 | Connolly et al. |
| 2019/0361051 A1 | 11/2019 | Vettori et al. |
| 2020/0078784 A1 | 3/2020 | Lowe et al. |
| 2021/0131966 A1 | 5/2021 | Connolly et al. |
| 2022/0042913 A1 | 2/2022 | Connolly et al. |

FOREIGN PATENT DOCUMENTS

| | | |
|---|---|---|
| JP | 2012/121748 A | 6/2012 |
| JP | 2013/503352 A | 1/2013 |
| JP | 2014/095025 A | 5/2014 |
| JP | 2016/188828 A | 11/2016 |
| JP | 2017/075964 A | 4/2017 |
| WO | WO-2008/004572 A1 | 1/2008 |
| WO | WO-2008/030960 A2 | 3/2008 |
| WO | WO-2008/044214 A1 | 4/2008 |
| WO | WO-2010051580 A1 | 5/2010 |
| WO | WO-2011/026030 A1 | 3/2011 |
| WO | WO-2011133632 A1 | 10/2011 |
| WO | WO-2013004852 A2 | 1/2013 |
| WO | WO-2013059404 A1 | 4/2013 |
| WO | WO-2014/108185 A1 | 7/2014 |
| WO | WO-2015/199940 A1 | 12/2015 |
| WO | WO-2016/118791 A1 | 7/2016 |
| WO | WO-2018075913 A1 | 4/2018 |
| WO | WO-2019/027917 A1 | 2/2019 |
| WO | WO-2021/096725 A1 | 5/2021 |

OTHER PUBLICATIONS

International Search Report and Written Opinion for International Application No. PCT/US2020/058664 dated Feb. 25, 2021.
Steen et al., "Magnetic interactions between nanoparticles," Beilstein Journal of Nanotechnology, 1: 182-190 (2010).
Extended European Search Report for EP Application No. 17884358.7 dated Jun. 22, 2020.
International Search Report and Written Opinion for International Application No. PCT/US2018/044409 dated Nov. 16, 2018.
Lai et al., "Influence of a static magnetic field on the photoluminescence of an ensemble of nitrogen-vacancy color centers in a diamond single-crystal," Applied Physics Letter, 95: Article 133101 (2009).
Shi et al., "Sensing and atomic-scale structure analysis of single nuclear-spin clusters in diamond," Nature Physics, 10: 21-25 (2013).
International Search Report and Written Opinion for International Application No. PCT/US2017/068126 dated Apr. 16, 2018.
Extended European Search Report for EP Application No. EP 17861549 dated Oct. 10, 2019.
Rondin et al., "Magnetometry with nitrogen-vacancy defects in diamond," Reports on Progress in Physics, 77(5):56503 (2014).
Schonfeld, "Optical readout of single spins for quantum computing and magnetic sensing," Fachbereich Physik der Freien Universitat Berlin eingereichte Dissertation 1-143 (2011).
Glenn et al., "Single-cell magnetic imaging using a quantum diamond microscope," Nature Methods, 12:736-738 (2015).
Hong et al., "Nanoscale magnetometry with NV centers in diamond," MRS Bulletin, 38:155-161 (2013).
Le Sage et al., "Optical magnetic imaging of living cells," Nature, 496:486-489 (2013).
Pham, "Magnetic Field Sensing with Nitrogen-Vacancy Color Centers in Diamond," Harvard University, Doctoral Dissertation (2013).
Taylor et al., "High-sensitivity diamond magnetometer with nanoscale resolution," Nature Physics, 4:810-816 (2008).
English Translation of Refusal Notice for JP Application No. 2019/534665 dated Oct. 26, 2021.
Extended European Search Report for EP Application No. 18842062.4 dated Mar. 29, 2021.

(56) References Cited

OTHER PUBLICATIONS

Issadore et al., "Magnetic sensing technology for molecular analyses," Lab on a Chip, 14(14):2385-2397 (2014).

* cited by examiner

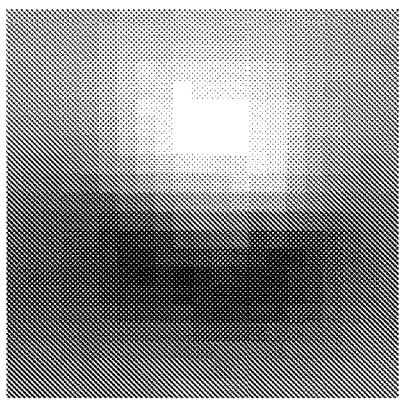
FIG. 11C-1 dimer #3
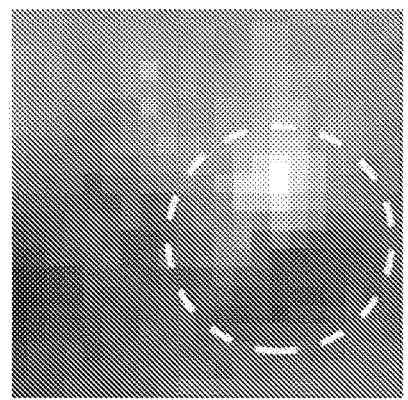
FIG. 11C-2
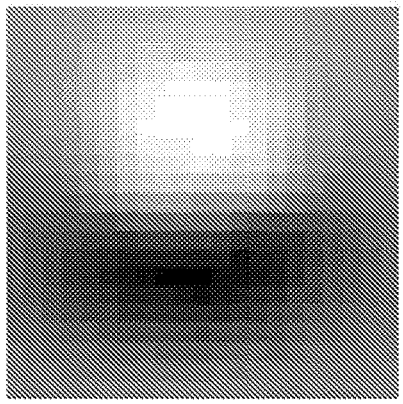
FIG. 11B-1 dimer #2
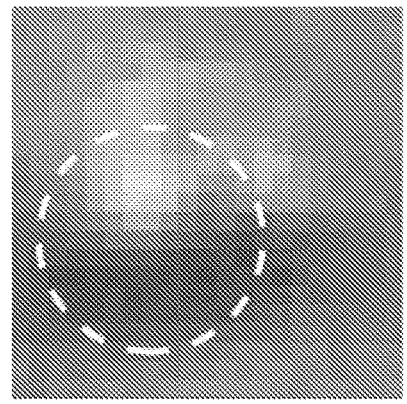
FIG. 11B-2
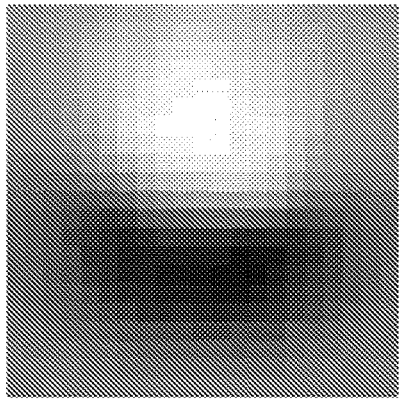
FIG. 11A-1 dimer #1
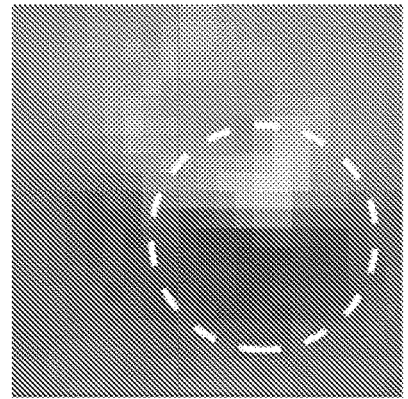
FIG. 11A-2
image signal
difference signal

METHODS AND APPARATUS FOR MAGNETIC MULTI-BEAD ASSAYS

CROSS REFERENCE TO RELATED APPLICATION

This application is a national stage application, filed under 35 U.S.C. § 371, of International Patent Application No. PCT/US17/68126 filed on Dec. 22, 2017 entitled METHODS AND APPARATUS FOR MAGNETIC MULTI-BEAD ASSAYS, which claims the benefit of U.S. Provisional Patent Application No. 62/438,593 filed on Dec. 23, 2016 entitled METHODS AND APPARATUS FOR MAGNETIC MULTI-BEAD ASSAYS. The entire contents of the above applications are incorporated herein by reference in their entirety.

GOVERNMENT SUPPORT

This invention was made with government support under contract number HR0011-14-C-0020 awarded by the Defense Advanced Research Projects Agency of the Department of Defense. The government has certain rights in the invention.

BACKGROUND

Enzyme linked immunosorbent assay (ELISA) has been an industry wide standard research technique used for measuring protein analytes from biological matrices since its introduction in the 1960s. In its basic conception, two antibodies (immunoglobulins) are used to capture a single protein analyte. The resulting immunocomplex is identified and measured using an enzyme and reporter buffer. The enzyme is typically bound to one of the antibodies through covalent binding. The enzyme, when incubated in the presence of the reporter buffer, converts the substrate to a functional reporter which can be measured analytically by spectrophotometric means.

Current state of the art ELISA-related technologies are replacing the plate-based format with a single-bead-based format. Single-bead-based ELISAs have one antibody that is bound to a solid surface, typically a bead, and the second antibody is labeled with biotin. The capture bead contains material that allows it to be easily manipulated by an applied magnetic field, including separating the bead and any analytes bound to the bead from a sample suspension. This process, called magnetic separation, is well known in the art and may be used to concentrate the target analyte and to remove unbound material such as unwanted proteins that may contribute to signal background. Compared to traditional ELISAs, single-bead-based ELISAs can provide improved sensitivity to target analytes with lower background and in a shorter amount of time.

Nevertheless, there is a need for continuing improvement in sensitivity and specificity to target analytes.

BRIEF SUMMARY

Various embodiments disclosed herein relate to methods and apparatus for detecting a complex including an analyte in a sample by observing complexes containing two or more distinguishable beads (i.e., beads of different types) that are bound by the analyte. In accordance with one or more embodiments, a bead-based magnetic assay system for detecting a complex including an analyte based on optically detected magnetic resonance (ODMR) includes a plurality of functionalized beads of a first type, which are magnetic functionalized beads and are functionalized to include a first moiety that associates with an analyte under suitable conditions, a plurality of functionalized beads of a second type, which are functionalized to include a second moiety that associates with the analyte under suitable conditions, a substrate including at least one ODMR center, a light source configured to generate incident light that excites electrons within the at least one ODMR center from a ground state to an excited state, a magnet for applying a bias magnetic field on a complex disposed over the at least one ODMR center, the complex including one of the first type of functionalized bead, the analyte, and one of the second type of functionalized bead. The system further includes a microwave source configured to generate a microwave field incident on the at least one ODMR center, the microwave source being further configured to generate the microwave field with frequencies that correspond to ground state transitions in the at least one ODMR center, in which the at least one ODMR center produces emitted light when illuminated by the incident light, characteristics of the emitted light being influenced by the microwave field and by the magnetic functionalized bead associated with the analyte in the complex, and an optical photodetector that detects light emitted by the at least one ODMR center. In some embodiments, the at least one ODMR center can be a silicon vacancy center in a silicon carbide lattice. In other embodiments, the at least one ODMR center can be a silicon vacancy center in a diamond lattice. In still other embodiments, the at least one ODMR center can be a nitrogen-vacancy center in a diamond lattice. In certain embodiments, the at least one ODMR center can be formed in an upper surface of the substrate. In some embodiments, the at least one ODMR center can be a plurality of ODMR centers formed in the upper surface of the substrate. In these embodiments, the optical photodetector can be an optical imaging system having an imaging sensor that images the emitted light from the plurality of ODMR centers. In certain embodiments, each of the first and the second moiety can be a receptor, protein, antibody, cell, virus, or nucleic acid sequence. In some embodiments, the functionalized beads of the first type can be superparamagnetic functionalized beads including a superparamagnetic material. In certain embodiments, the functionalized beads of the first type can include a nonmagnetic layer encapsulating the superparamagnetic material. In some embodiments, the superparamagnetic functionalized beads can include iron oxide particles. In certain embodiments, the functionalized beads of the first type can comprise magnetic nanoparticles disposed within a polymer substrate. In other embodiments, the functionalized beads of the first type can comprise magnetic nanoparticles disposed on a surface of a polymer substrate. In some embodiments, the functionalized beads of the second type can be fluorescent functionalized beads. In other embodiments, the functionalized beads of the second type can be magnetic functionalized beads including a quantity of magnetic material distinguishable from the functionalized beads of the first type. In still other embodiments, the functionalized beads of the second type can be magnetic functionalized beads, the second type of functionalized beads including a magnetic property distinguishable from the functionalized beads of the first type. In some embodiments, the functionalized beads of the first type can be superparamagnetic functionalized beads including a superparamagnetic material. In certain embodiments, the functionalized beads of the first type can include a nonmagnetic layer encapsulating the superparamagnetic material. In some embodiments, the functionalized beads of the second type can be ferromagnetic functionalized beads including a ferromagnetic material. In certain embodiments, the functionalized beads of the second type can include a nonmagnetic layer encapsulating the ferromagnetic material. In some embodiments, each of the first type of functionalized beads and the second type of functionalized beads can have a diameter in a range of between 50 nm and 10 µm. In certain embodiments, each of the diameters of the functionalized beads of the first type and the second type can be in a range of between 0.5 µm and 5 µm. In some embodiments, the diameter of the functionalized beads of the first type can be similar to the diameter of the functionalized beads of the second type. In other embodiments, the diameter of the functionalized beads of the first type can be different from the diameter of the functionalized beads of the second type by at least 50%. In some embodiments, the system can further include a plurality of functionalized beads of at least a third type, functionalized to include at least the second moiety that associates with at least a second analyte under suitable conditions. In certain embodiments, the system can further include a plurality of functionalized beads of a fourth type, functionalized to include the second moiety that associates with the second analyte under suitable conditions. In some embodiments, the functionalized beads of the first and/or second type can further include at least one additional moiety that associates with the second analyte under suitable conditions. In certain embodiments, the system can further include a third moiety that associates with a third analyte under suitable conditions, wherein the functionalized beads of the first type are further functionalized to include the second moiety, and the functionalized beads of the second type are further functionalized to include the third moiety.

In accordance with one or more embodiments, a method of detecting a complex including an analyte includes contacting a sample in a solution with a population of functionalized beads of a first type, which are magnetic functionalized beads and are functionalized to include a first moiety that associates with an analyte under suitable conditions, contacting the sample solution with a population of functionalized beads of a second type, which are functionalized to include a second moiety that associates with the analyte under suitable conditions, contact resulting in formation of a complex including one of the first type of functionalized bead, the analyte, and one of the second type of functionalized bead, and detecting the complex including the analyte by detecting magnetic fields produced by the magnetic functionalized bead and by detecting the functionalized bead of the second type associated with the analyte in the complex. In some embodiments, the method can further include disposing the sample solution including the complex over a substrate that includes at least one optically detected magnetic resonance (ODMR) center formed in the substrate, exciting electrons within the at least one ODMR center from a ground state to an excited state with incident light, applying a bias magnetic field on the complex, and generating a microwave field incident on the at least one ODMR center, the microwave field including frequencies that correspond to ground state transitions in the at least one ODMR center, wherein detecting the complex including the analyte further includes analyzing light emitted by the at least one ODMR center, characteristics of the emitted light being influenced by the microwave field and by the magnetic functionalized bead associated with the analyte in the complex. In some embodiments, the at least one ODMR center can be a nitrogen-vacancy center in a diamond lattice. In certain embodiments, the at least one ODMR center can be formed in an upper surface of the substrate. In some embodiments, the at least one ODMR center can be a plurality of ODMR centers formed in the upper surface of the substrate. In these embodiments, analyzing light emitted by the plurality of ODMR centers includes imaging the emitted light. In certain embodiments, the method can further include applying a magnetic field gradient to the sample solution after contacting the sample with the population of functionalized beads of the first type. In some embodiments, applying the magnetic field gradient to the sample solution can be performed after contacting the sample solution with the population of functionalized beads of the second type. In certain embodiments, the population of functionalized beads of the first type and the population of functionalized beads of the second type can be added to the sample solution sequentially. In some embodiments, the functionalized beads of the second type can be fluorescent functionalized beads, and the method can further include illuminating the complex with incident light that excites fluorescence within the functionalized beads of the second type and fluorescence imaging of the complex. In other embodiments, the functionalized beads of the second type can be magnetic functionalized beads, including a magnetic property distinguishable from the functionalized beads of the first type. In some embodiments, the method can further include applying a magnetic field gradient to the sample solution after contacting the sample solution with the functionalized beads of the first and second types. In certain embodiments, the method can further include varying the magnetic field gradient applied to the sample solution. In some embodiments, the method can further include concentrating the sample solution after contacting the sample solution with the population of functionalized beads of the second type. In certain embodiments, the method can further include agglomerating a plurality of functionalized beads of the first and second types, after contacting the sample solution with the population of functionalized beads of the second type, before detecting the complex. In some embodiments, the method can further include dehydrating the sample solution after disposing the sample solution over the diamond substrate.

In accordance with one or more embodiments, a bead-based assay system for detecting a complex including an analyte includes a plurality of functionalized beads of a first type, which are magnetic functionalized beads and are functionalized to include a first moiety that associates with an analyte under suitable conditions, a plurality of functionalized beads of a second type, which are fluorescent functionalized beads, and are functionalized to include an unlabeled moiety that associates with the analyte under suitable conditions, a light source configured to generate incident light that excites fluorescence within the functionalized beads of the second type, and an optical fluorescence detector that detects fluorescence emitted by the functionalized beads of the second type associated with the analyte in a complex including one of the first type of functionalized bead, the analyte, and one of the second type of functionalized bead. In certain embodiments, the fluorescent functionalized beads can comprise a polymer substrate impregnated with a fluorescent material. In some embodiments, the optical fluorescence detector can include a spectrophotometer. In other embodiments, the optical fluorescence detector can include an optical imaging sensor that images the fluorescence emitted by the functionalized beads of the second type associated with the analyte in the complex. In some embodiments, the functionalized beads of the first type can be superparamagnetic functionalized beads. In certain embodiments, the superparamagnetic functionalized beads can include iron oxide particles. In some embodiments, the functionalized beads of the first type can include magnetic nanoparticles disposed within the polymer substrate. In other embodiments, the functionalized beads of the first type can include magnetic nanoparticles disposed on a surface of the polymer substrate.

In accordance with one or more embodiments, a method of detecting a complex including an analyte includes contacting a sample in a solution with a population of functionalized beads of a first type, which are magnetic functionalized beads and are functionalized to include a first moiety that associates with an analyte under suitable conditions, contacting the sample solution with a population of functionalized beads of a second type, which comprise a polymer substrate impregnated with a fluorescent material, and are functionalized to include an unlabeled moiety that associates with the analyte under suitable conditions, contact resulting in formation of a complex including one of the first type of functionalized bead, the analyte, and one of the second type of functionalized bead, illuminating the complex with incident light that excites fluorescence within the functionalized beads of the second type, and detecting the complex including the analyte by analyzing fluorescence emitted by the functionalized beads of the second type associated with the analyte in the complex. In some embodiments, the method can further include applying a magnetic field gradient to the sample solution after contacting the sample with the population of functionalized beads of the first type. In certain embodiments, applying the magnetic field gradient to the sample solution can be performed after contacting the sample solution with the population of functionalized beads of the second type. In some embodiments, the method can further include concentrating the sample solution after contacting the sample solution with the population of functionalized beads of the second type, before detecting the complex. In certain embodiments, the method can further include agglomerating a plurality of functionalized beads of the first and second types, after contacting the sample solution with the population of functionalized beads of the second type, before detecting the complex. In some embodiments, the method can further include dehydrating the sample solution before detecting the complex.

Magnetic multi-bead assays improve upon bead-based ELISAs by detecting target analytes bound in complexes, such as immunocomplexes. By combining the convenience and simplicity of magnetic separation with robust and sensitive detection of beads, magnetic multi-bead assays provide excellent sensitivity with a simple, rapid process.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 10A-2, 10B-2, and 10C-2 illustrate magnetic images of the difference signal after subtracting the characteristic signal of three beads B in accordance with one or more embodiments.

FIGS. 11A-1, 11B-1, and 11C-1 illustrate magnetic images of the image signal of three dimers of beads A and B in accordance with one or more embodiments.

FIGS. 11A-2, 11B-2, and 11C-2 illustrate magnetic images of the difference signal of three dimers beads A and B after subtracting the characteristic bead B signal in accordance with one or more embodiments.

DETAILED DESCRIPTION

Figure 1A:
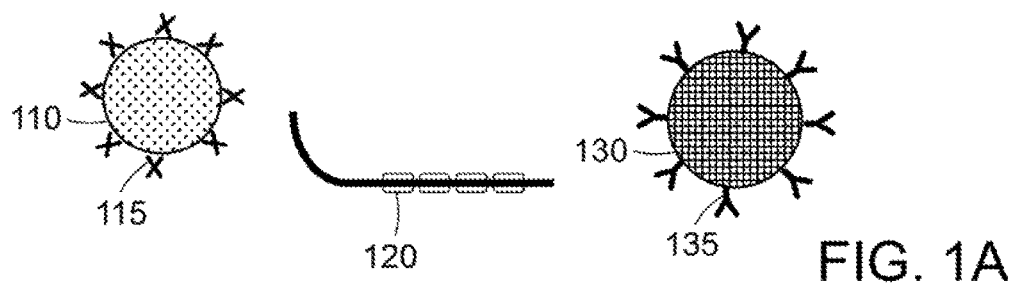
FIG. 1A schematically illustrates a functionalized bead of a first type, a first moiety, a functionalized bead of a second type, a second moiety, and an analyte in accordance with one or more embodiments.

As stated above, various embodiments disclosed herein relate to methods and apparatus for detecting a complex including an analyte in a sample by observing complexes containing two or more distinguishable beads (i.e., beads of different types) that are bound by the analyte. At least one of the bead types is magnetic and can be concentrated in a liquid suspension by means of magnetic forces exerted with an applied magnetic field. A fully-magnetic assay may also be implemented by using diamond magnetic imaging to distinguish between magnetic bead types with distinct magnetic properties.

In accordance with one or more embodiments, wide-field magnetic imaging using nitrogen-vacancy (NV) centers in diamond can be used to provide a platform on which to implement a multi-bead assay that is fully magnetic, eliminating the need to detect fluorescence from the sample. Magnetic beads provide strong, stable signals by means of the magnetic fields they produce, which permeate through biological sample matrices and contaminants and allow for unambiguous detection. Magnetic beads can further be manipulated to accelerate assay kinetics and enable rapid sample preparation with minimal hardware. The fully magnetic assay can be deployed with a small-footprint instrument and low reagent volumes, delivering rapid assay results at low cost.

Magnetic Multi-Bead Assays

Magnetic multi-bead assays make use of distinct bead types to determine analyte concentration in a sample by detecting the formation of bead complexes that are bound by the analyte. One bead type has magnetic properties that allow for separation of beads and bound material from a suspension of beads in liquid with the application of a magnetic field gradient. This process, called magnetic separation, is commonly used to isolate or concentrate target analytes, including cells, proteins, and nucleic acids.

The sensitivity of the magnetic multi-bead assay stems in part from three features:
(1) The assay measures co-presence of at least two distinguishable beads, such that detection of the target analyte only results from the analyte binding to at least two distinct antibodies on at least two distinguishable bead types. This assay provides enhanced target specificity through the combined specificity of multiple antibodies, which in turn provides better sensitivity.
(2) Confounding effects, such as signal backgrounds, caused by sample components other than the target analyte can be reduced or eliminated by purifying the sample using magnetic separation.
(3) Beads can be detected rapidly and with high accuracy and precision. Bead signals can be stronger and more stable and can be detected more quickly than signals from molecular reporters including fluorescent dyes and fluorescent products of enzymatic activity.

Complex Formation

To measure a target analyte in a multi-bead assay, the analyte must bind to at least two distinguishable beads to form a complex, so that the presence of both beads can be detected. The beads may be coated with binding ligands, herein also denoted as moieties, such as antibodies, that bind specifically to and thereby associate with a certain region of a certain target analyte. Each bead in the multi-bead assay may be coated with one or more different types of binding ligands. Different bead types used in the multi-bead assay may have the same binding ligand types, overlapping sets of binding ligand types, or distinct binding ligand types. In the simplest case, two distinct bead types are used—hereafter denoted bead A and bead B. (In other embodiments, three or more distinct bead types can be used.) In the two-bead example, bead A and bead B are coated with antibodies, with antibody X on bead A and antibody Y on bead B. Antibody X binds specifically to a different region of the target analyte than antibody Y so that the target analyte may be bound to both simultaneously.

The complex, such as an immunocomplex, may be formed under suitable conditions, such as by incubating the sample with a suspension of bead A and bead B. Target analytes in the sample will encounter a bead surface as they diffuse through the sample, and bind to it. The sample may be mixed, shaken, or otherwise agitated to accelerate this process. As the beads also move through the sample, they will encounter analytes bound to beads of the opposite type and will additionally bind to those analytes, forming heterogeneous bead complexes of the form A-B, A-B-A, B-A-B, and other combinations.

The beads and bead complexes are then concentrated together by magnetic separation. First, a magnetic field gradient is applied that exerts a magnetic force on bead A. Any bead A and bead complex containing bead A will be separated from the sample. In some embodiments, bead B may also be magnetic and experience a similar magnetic force, forming a "pellet" of magnetic material and bound analytes. Unbound sample components, referred to here as "background material," will not be separated and therefore may be discarded with the supernatant above the pellet. The magnetic gradient may then be removed and the beads may be re-suspended in the same or different buffer solution. This process may be repeated to reduce the concentration of background material. Magnetic separation may be performed by hand or automated with a commercial plate washer.

Alternately, complex formation can also be performed in discrete steps, which may reduce signal background caused by nonspecific binding of beads into complexes in the absence of the target analyte. Bead A may first be added to the sample to capture the target analyte, followed by magnetic separation to reduce the concentration of background material. Bead B can then be added separately to this purified sample. Whether bead A and bead B are added together or sequentially will be determined empirically and will depend on the antibodies utilized and whether nonspecific binding is significantly reduced using sequential binding steps.

If bead B is less magnetic than bead A, or nonmagnetic, then magnetic separation may be used after forming complexes to reduce signal background associated with unbound bead B. For example, a less-magnetic bead B will be separated from the sample suspension more slowly than bead A, so that magnetic separation can be terminated at a point at which bead A has been suitably separated into a pellet while the separation of bead B remains incomplete. If at this point the supernatant above the pellet is discarded, a significant fraction of bead B will be removed, but bead A will be preserved, including complexes containing bead A.

In accordance with one or more embodiments, the diameters of bead A and bead B may be in a range of between 50 nm and 10 µm, such as between 0.5 µm and 5 µm. Bead A and bead B may be chosen to have different diameters, such that the diameter of the functionalized beads of the first type is different from the diameter of the functionalized beads of the second type by at least 50%, so that the two bead types may be distinguished by the spatial distribution of their respective magnetic field signals. Alternatively bead A and bead B may be chosen to have similar diameters, that is, diameters different by less than 50%, so that they exhibit similar surface area, move similarly in the liquid sample suspension, occupy a similar amount of space in the detection region, and provide similar signal magnitudes. Bead diameters in the range of 0.5 µm to 5 µm may allow for rapid magnetic separation (in a matter of seconds) and a large quantity of binding ligands on each bead. In addition, bead diameters in this range are similar to or slightly larger than the typical diffraction-limited imaging resolution of an optical microscope or wide-field diamond magnetic imaging system.

Complex Detection

Once complexes, such as immunocomplexes, have been formed (heterogeneous bead complexes containing bead A and bead B bound by the analyte), they are measured by detecting the co-presence of both bead types. Several methods of detecting the co-presence of both bead types that can be implemented to achieve this goal are described further below.

The measurement of complexes containing the analyte can be calibrated with a range of calibration samples of known analyte concentration so that a given measurement of complexes implies a certain analyte concentration. The measurements of the range of calibration samples is collectively referred to as a calibration curve. Detection of complexes, by the methods and apparatus described herein, enables measuring analyte concentration in combination with a calibration curve.

Example A1: Magnetic-Fluorescent Assay with Plate Reader

Consider bead A to be superparamagnetic, composed of magnetic nanoparticles of a superparamagnetic material dispersed within or on the surface of a polymer substrate. Suitable superparamagnetic materials include, for example, iron oxide, $Fe_2O_3$ or $Fe_3O_4$, manganese ferrites ($MnFe_2O_4$), or cobalt ferrites ($CoFe_2O_4$), in the form of single crystal nanoparticles less than about 20 nm in size, typically in a range of between 5 nm and 10 nm. The magnetic nanoparticles are engineered to be small enough that they exhibit no remanent magnetization in the absence of an applied field (superparamagnetism). When a field is applied, the particles magnetize in the direction of the field, producing a bead magnetization sufficient for magnetic separation.

Consider bead B to be a fluorescent functionalized bead including a polymer substrate impregnated with fluorescent material. Bead B is nonmagnetic, such that unbound bead B is left behind during magnetic separation.

Figure 1B:
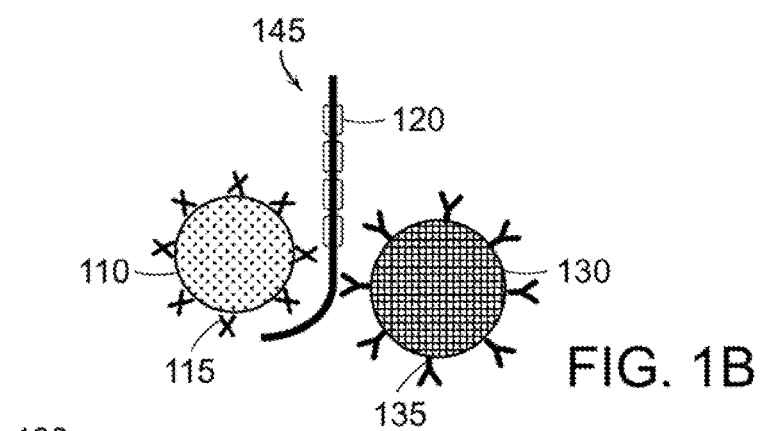
FIG. 1B schematically illustrates a complex that includes one of a functionalized bead of a first type, a first moiety, one of a functionalized bead of a second type, a second moiety, and an analyte in accordance with one or more embodiments.
Figure 1C:
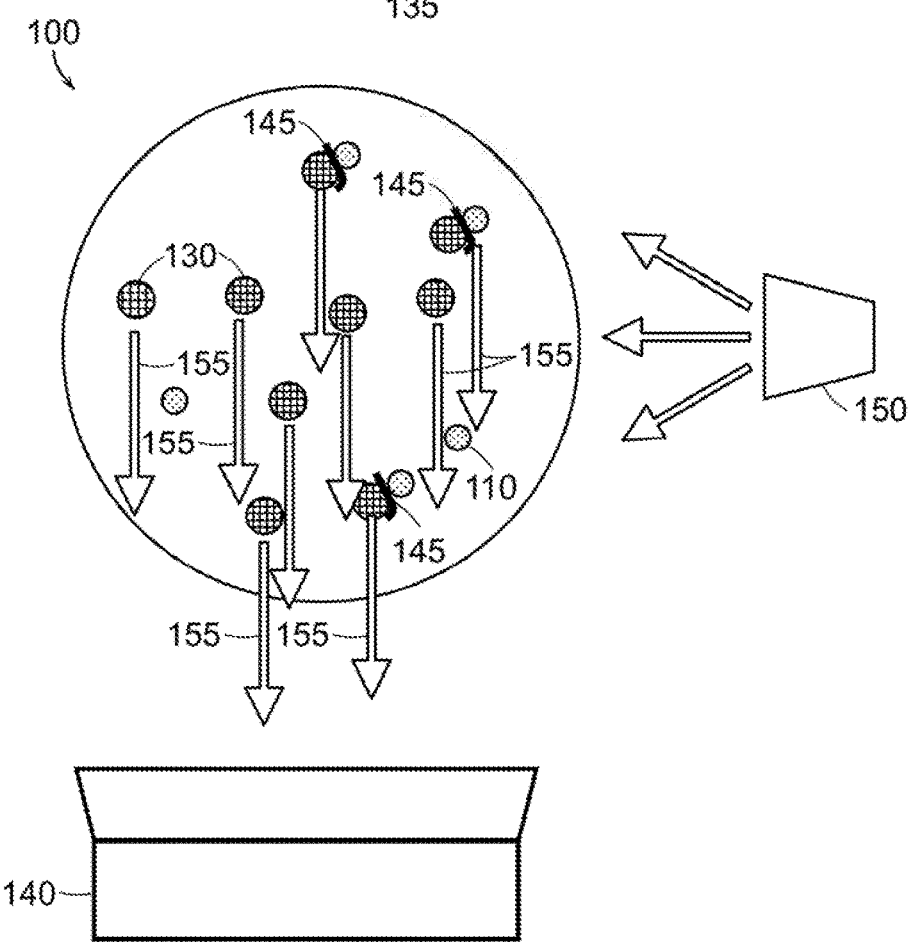
FIG. 1C schematically illustrates a bead-based assay system for detecting a complex including a spectrophotometer that detects fluorescence emitted by the functionalized beads of the second type in accordance with one or more embodiments.

As shown in FIGS. 1A-1C, a bead-based assay system 100 for detecting a complex including an analyte, shown in FIG. 1C, includes, as shown in FIG. 1A, a plurality of functionalized beads 110 of a first type (bead A), which are magnetic functionalized beads and are functionalized to include a first moiety X 115 that associates with an analyte 120 under suitable conditions, a plurality of functionalized beads 130 of a second type (bead B), which are fluorescent functionalized beads, and are functionalized to include an unlabeled moiety Y 135 that associates with the analyte 120 under suitable conditions, and, as shown in FIG. 1C, an optical photodetector 140 that detects light 155 emitted by the functionalized beads 130 of the second type associated with the analyte 120 in a complex 145, shown in FIG. 1B, including the first type of functionalized bead 110, the analyte 120, and the second type of functionalized bead 130. As shown in FIG. 1C, the optical photodetector 140 is a spectrophotometer 140 that detects fluorescence 155 emitted by the functionalized beads 130 of the second type that fluoresce when illuminated by light from a filtered lamp 150. Each of the first 115 and second 135 moiety can be a receptor, protein, antibody, cell (eukaryotic or prokaryotic), organelle, virus, or nucleic acid sequence. The second moiety 135 is unlabeled, that is, not labeled with a fluorophore. In some embodiments, the fluorescent functionalized beads can comprise a polymer substrate impregnated with a fluorescent material. Several improvements arise from having the fluorescent material impregnated inside the functionalized beads B and using an unlabeled second moiety 135. First, the volume of the bead allows for much greater quantities of fluorophores to be included and measured, as compared to surface attachment, because the volume of the bead is significantly greater than its surface area. Second, in other methods whereby the surface bound moiety is labeled with a fluorophore, the quantity of fluorophore is further reduced as the moieties do not cover the entire surface, resulting in even further reduced labeling. Third, fluorophores are sensitive to light, temperature, pH, salt and other environmental conditions associated with biological assays. As such, the fluorophores impregnated into the bead are sheltered and protected from the chemical environment, which results in brighter and more robust detection. Fourth, for fluorophores to be conjugated or covalently bound to surface attached moieties, they must undergo a chemical reaction that can alter the state of the fluorophore (such as its 3D structure, charge, polarity) that can negatively affect the function of the fluorophore.

Due to the superparamagnetic nature of the capture bead A, extra bead A will be included in the final read. However, since this bead is in a different fluorescent channel (wavelength) or not fluorescent at all, it will not negatively affect the positive signal of the detector bead B or provide additional non-specific (fluorescent) background.

In one embodiment, the magnetic multi-bead assay is performed as described below. After complex formation, a magnetic separation step or series of repeated steps is used to reduce the unbound bead B population. After magnetic separation, the continued presence of bead B indicates successful binding of the target analyte both to bead A and to bead B—otherwise either the analyte or bead B or both would likely have been discarded during magnetic separation. Detecting bead B in the sample suspension is therefore sufficient to establish co-presence of both beads in complexes.

Figure 2:
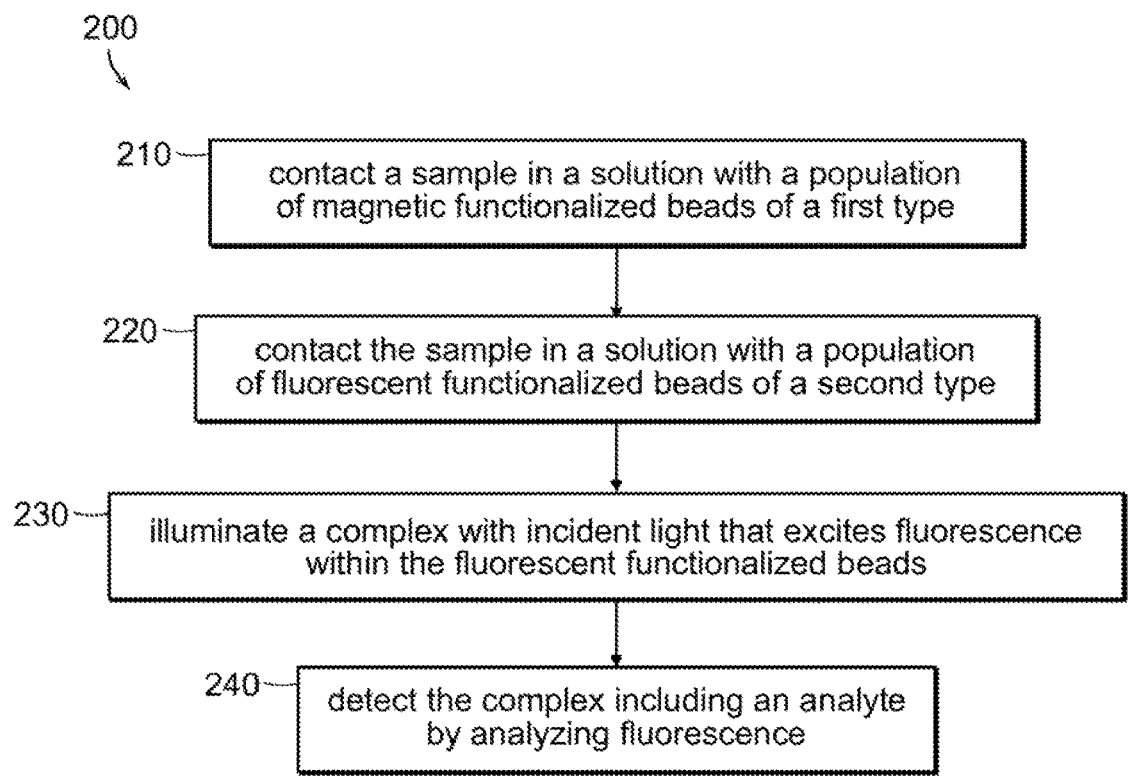
FIG. 2 illustrates a method of detecting a complex including an analyte in accordance with one or more embodiments.

Accordingly, as shown in FIG. 2, a method 200 of detecting a complex including an analyte includes contacting 210 a sample in a solution with a population of magnetic functionalized beads of a first type, contacting 220 the sample solution with a population of fluorescent functionalized beads of a second type, illuminating 230 the complex with incident light that excites fluorescence within the functionalized beads of the second type, and detecting 240 the complex including the analyte by analyzing the fluorescence.

The sample suspension may be analyzed using a fluorescent plate reader or similar device that uses a spectrophotometer to optically excite and measure fluorescence from each plate well. The suspension may be transferred to low-fluorescence black plates prior to measurement to reduce signal background produced by the plate. While it is possible that the reactions could be performed in the black plates originally, reactions may be more efficiently performed in round-bottom plates that may be unavailable in black plastic. During the fluorescence measurement, bead B fluorescence may be both induced and recorded through optical band pass filters. A titration of bead B and a well containing no bead B may be separately measured to calibrate the observed fluorescence signal to a known bead concentration under similar buffer conditions.

Most commercially available fluorescent plate readers can be configured with standard excitation and emission filters, dichroic or band pass filters, and proper gain settings or photo multiplier tube (PMT) adjustments to satisfactorily depress autofluorescence of sample buffer and amplify true fluorescent signal from the ensemble fluorescent beads. The wavelength of measured fluorescence will depend upon the choice of fluorophore incorporated into the bead. It should be noted that low fluorophore concentration or weak fluorophores may depress the fluorescent signal and reduce the sensitivity of the assay.

Figure 1D:
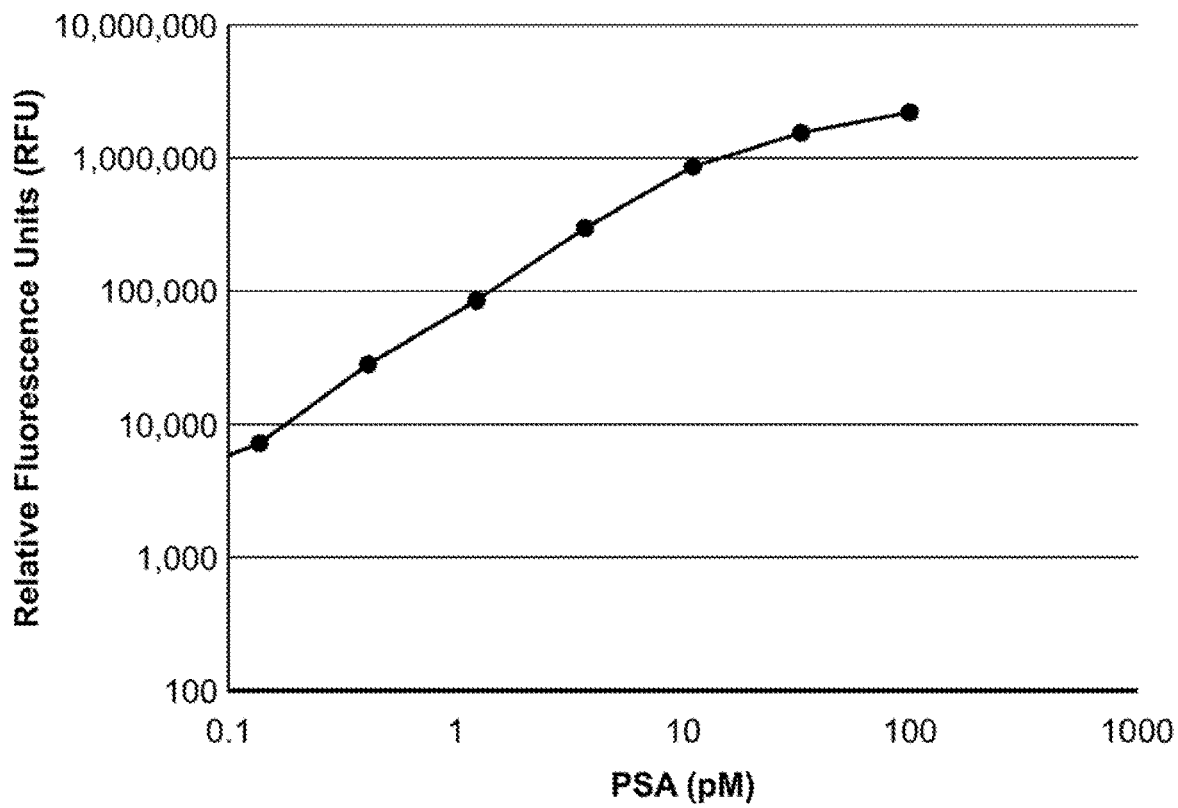
FIG. 1D illustrates a plot of relative fluorescence units (RFU) as a function of PSA (pM) in accordance with one or more embodiments.

As shown in FIG. 1D, prostate specific antigen (PSA) as low as 0.1 pg/mL can be measured with little optimization of the plate reader conditions. As few as 250 fluorescent beads can be measured at the minimum signal level, considered to be the fluorescence measurement background mean plus triple its standard deviation. Longer read times, changes in photomultiplier tube (PMT) gain settings, or adjustments in the scanned region of each well all may contribute to improved sensitivity. Optimization of these parameters depends upon the features of any given plate reader.

Example B2: Magnetic-Fluorescent Assay with Fluorescence Imaging

Consider bead A and bead B to be of the same types described in Example A1 above. Further consider that, as in Example A1, a final magnetic separation step or series of steps is performed to reduce the concentration of bead B.

Figure 3A:
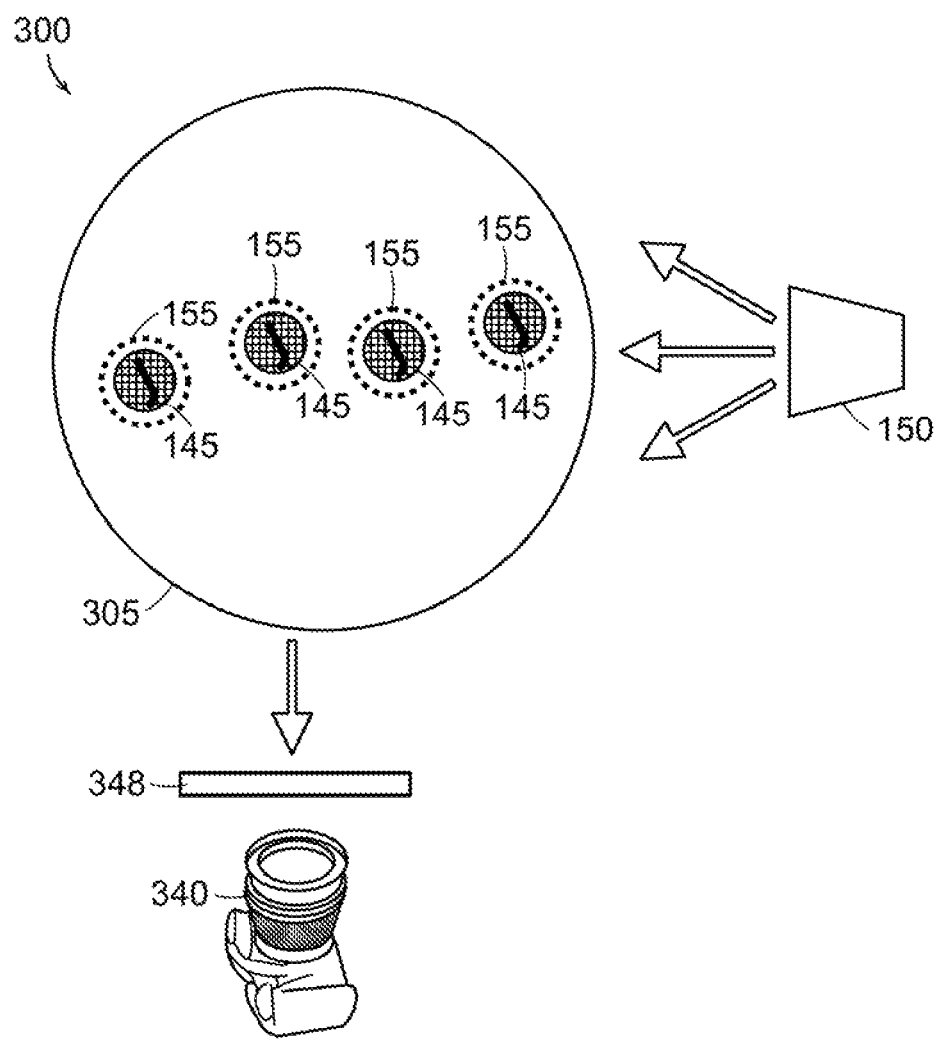
FIG. 3A schematically illustrates a bead-based assay system for detecting a complex including an optical imaging sensor that images fluorescence emitted by the functionalized beads of the second type in accordance with one or more embodiments.
Figure 3B:
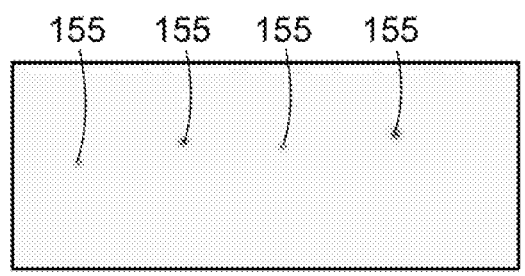
FIG. 3B illustrates a fluorescent image in accordance with one or more embodiments.

In another embodiment employing a bead-based assay system 300, shown in FIG. 3A, bead B fluorescence may be measured by fluorescence imaging rather than with a spectrophotometer. The sample suspension or a portion of it may be dispersed on a microscope slide 305. Under appropriate optical excitation, bead B fluorescence may be imaged by a microscopy system onto a camera sensor 340 through an optical band pass filter 348 that blocks the excitation light from the filtered lamp 150. In the resulting bead B fluorescence image, and provided suitable resolution of the microscopy system, individual beads may be resolved, identified, and counted (as illustrated in FIG. 3B). The total number of beads B counted in the image provides a measurement of the number of analytes present in the sample, since the observation of bead B fluorescence 155 implies co-presence of both bead A and bead B bound to the target analyte in the complex 145.

Fluorescence imaging may provide an improvement in sensitivity above the plate reader measurement described above in Example A1. This improvement arises from the ability to reject confounding signals, including:

(1) optical detector backgrounds, such as arise from optical filter leakage and optical sensor noise;

(2) diffuse fluorescence backgrounds, such as autofluorescence from buffer components;

(3) fluorescence from contaminants, such as dust particles, that may be clearly distinguished in images from bead B signals.

Figure 3C:
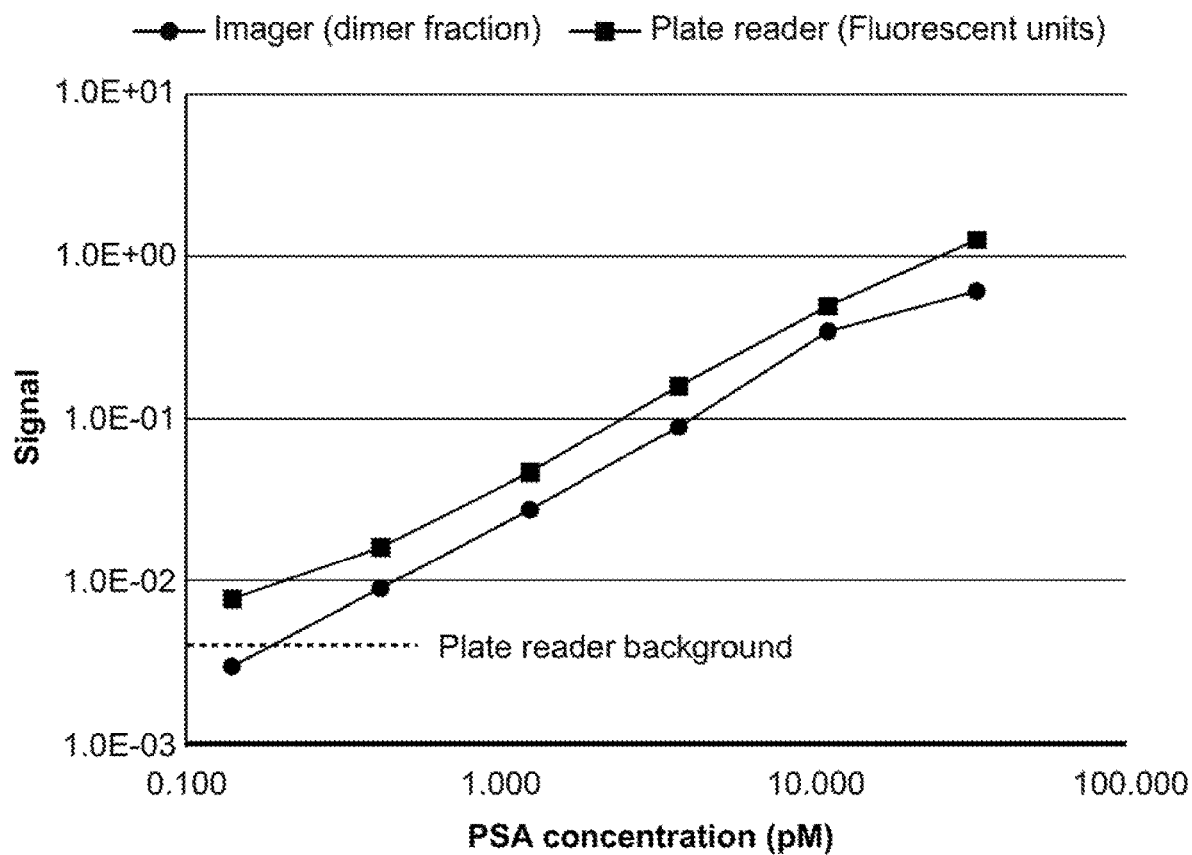
FIG. 3C illustrates a plot of signal as a function of PSA concentration (pM) in accordance with one or more embodiments.

Rejecting false signals allows for a lower signal background, as shown in FIG. 3C, where the imager 340 yields a lower signal level for the same PSA concentration as compared to the plate reader 140, and a correspondingly improved sensitivity to low complex concentrations that result from low analyte concentrations.

Imaging of bead B may be performed with a liquid sample suspension, such as a droplet on a microscope slide under a coverslip, or after drying a representative droplet of the liquid sample. After drying, fluorescent bead B remains bright and no longer moves under diffusion or due to flow of the sample on the slide, which enables longer exposure times and lower excitation light intensity. The buffer solution is chosen to preserve immunocomplexes against dissociation during drying, to disperse beads relatively uniformly over the dried region, and to avoid leaving solute crystals or other residue that may impede imaging.

Example C3: Magnetic-Fluorescent Assay with Magnetic and Fluorescence Imaging

Consider bead A and bead B to be of the same types described in Example A1 above. Further consider that, as in Example A1, a final magnetic separation step or series of steps is performed to reduce the concentration of bead B and that bead B is counted by imaging the sample with a fluorescence microscopy system.

Figure 4:
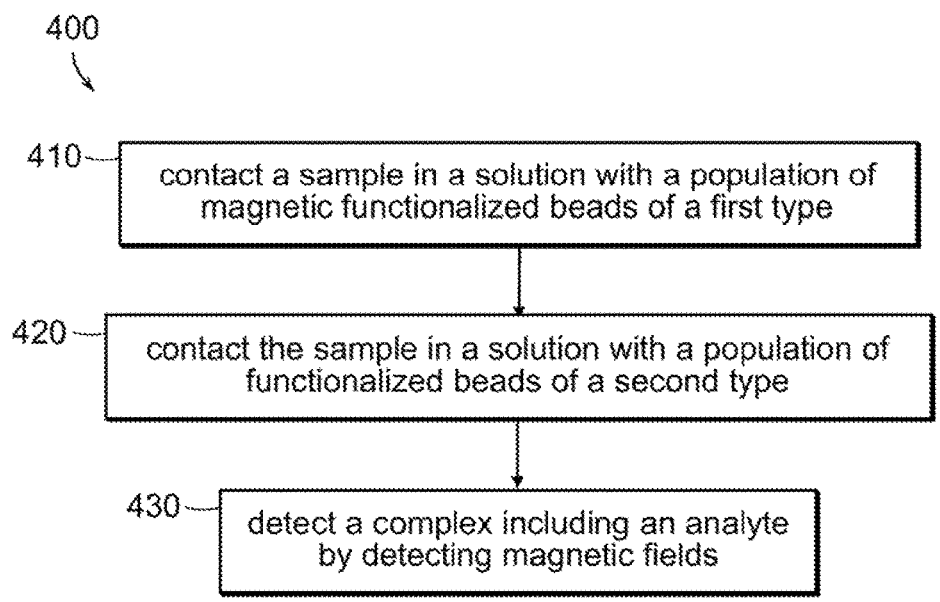
FIG. 4 illustrates another method of detecting a complex including an analyte in accordance with one or more embodiments.

In accordance with one or more embodiments, as shown in FIG. 4, a method 400 of detecting a complex including an analyte includes contacting 410 a sample in a solution with a population of magnetic functionalized beads of a first type, contacting 420 the sample solution with a population of functionalized beads of a second type, and detecting 430 the complex including the analyte by detecting magnetic fields produced by the magnetic functionalized bead and by detecting the functionalized bead of the second type associated with the analyte in the complex. In some embodiments, detecting magnetic fields includes using any magnetic imaging technology, such as magnetic force microscopy or a scanning Hall probe. In certain embodiments, detecting the functionalized beads of the second type includes detecting fluorescence as described in Examples A1 or B2 above.

In another embodiment, the microscopy system may include a wide-field diamond magnetic imaging system that allows for imaging of bead A, which is superparamagnetic. Wide-field diamond magnetic imaging with nitrogen-vacancy (NV) centers in diamond is capable of rapidly imaging magnetic fields disposed over the surface of a diamond sensor, at room temperature, with sub-micron resolution. Magnetic images may be co-registered to conventional optical fluorescence or bright-field images acquired for the same field of view with the same imaging system. Adjustments to the imaging system may be made between magnetic and optical imaging to optimize performance, such as changing optical filters or correcting focal position.

Figure 5:
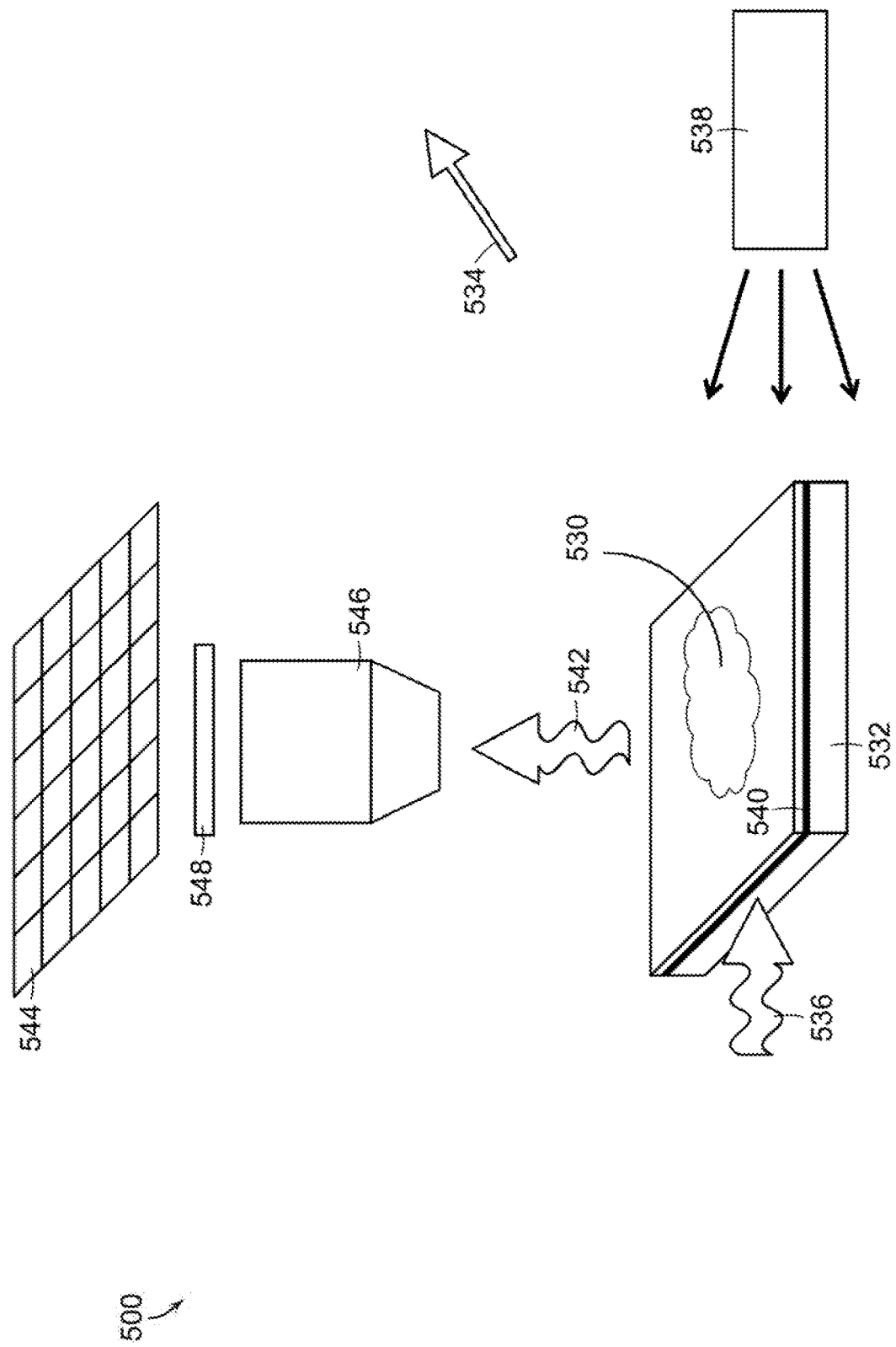
FIG. 5 schematically illustrates a wide-field diamond magnetic imaging apparatus in accordance with one or more embodiments.

As shown in FIG. 5, a bead-based magnetic assay system 500 for detecting a complex including an analyte based on optically detected magnetic resonance (ODMR) includes, as shown in FIG. 1A and described above, a plurality of functionalized beads 110 of a first type, which are magnetic functionalized beads and are functionalized to include a first moiety 115 that associates with an analyte 120 under suitable conditions, a plurality of functionalized beads 130 of a second type, which are functionalized to include a second moiety 135 that associates with the analyte 120 under suitable conditions, and, as shown in FIG. 5, a substrate 532 including at least one ODMR center 540 (a plurality of ODMR centers 540 shown in FIG. 5), a light source 536 configured to generate incident light that excites electrons within the at least one ODMR center 540 from a ground state to an excited state, a magnet 534 for applying a bias magnetic field on a complex 530 disposed over the at least one ODMR center 540, the complex 530 including one of the first type of functionalized bead 110, the analyte 120, and one of the second type of functionalized bead 130, and a microwave source 538 configured to generate a microwave field incident on the at least one ODMR center 540, the microwave source 538 being further configured to generate the microwave field with frequencies that correspond to ground state transitions in the at least one ODMR center 540, in which the at least one ODMR center 540 produces emitted light 542 when illuminated by the incident light 536, characteristics of the emitted light 542 being influenced by the microwave field and by the magnetic functionalized bead 110 associated with the analyte 120 in the complex 330. In the embodiment shown in FIG. 5, the plurality of ODMR centers 540 are nitrogen-vacancy (NV) centers in a diamond lattice, formed in an upper surface of the diamond substrate 532. In another aspect, the plurality of ODMR centers can be silicon-vacancy centers in a silicon carbide lattice, or in a diamond lattice. Turning back to FIG. 5, under optical excitation 536, fluorescence 542 emitted from a thin layer of ODMR centers 540 near the surface of the diamond substrate 532 is imaged onto an optical photodetector array 544, that is an optical imaging system having an imaging sensor such as a charge-coupled device (CCD) or complementary metal oxide semiconductor (CMOS) camera. The variation of ODMR center fluorescence under microwave excitation reveals the ODMR electron spin resonance (ESR) frequency, and hence the magnetic field shift of the ODMR spin sublevels. The spatial structure of the magnetic field at the diamond surface created by the sample (i.e., complex) 530 can thus be determined from images of ODMR center fluorescence 542, whose characteristics are influenced by the microwave field and by the magnetic field created by the magnetic functionalized bead 110 associated with the analyte 120 in the complex 530.

Briefly, the process to acquire a magnetic image is as follows:

1. Dispose a magnetic sample (i.e., complex) 530 to be imaged over, onto, or near to the sensing surface of the diamond substrate 532. An intermediate layer (not shown) may be interposed between the sample 530 and the diamond substrate 532.
2. Apply a magnetic bias field 534 in an arbitrary direction.
3. Illuminate the ODMR centers 540 in the diamond center with green light 536 (near 532 nm wavelength).
4. Apply a microwave field from a source 538 to the diamond, with frequency near one of the ODMR center ESR transitions.
5. Acquire an image of ODMR center fluorescence 542 emitted from the sensing surface 540 at optical detector array 544 through imaging objective 546 and optical filter 548.
6. Repeat steps 4-5 using different microwave frequencies that span one or more ranges around one or more NV center ESR transitions. The result is a stack of images, each corresponding to a different microwave frequency.
7. Repeat steps 4-6 one or more times, averaging the results to reduce imaging noise in the image stack.
8. For each image pixel in the image stack, construct an ESR spectrum from that pixel's value across all images in the stack. Analyze this spectrum to determine the frequencies of one or more ESR transitions.
9. For each image pixel in the image stack, compute the magnetic field based on the frequencies of observed ESR transitions at that pixel.

Additional details of the operation of the wide-field diamond magnetic imaging apparatus are described in PCT Patent Application No. PCT/US2017/057628 filed on Oct. 20, 2017 and entitled METHODS AND APPARATUS FOR MAGNETIC PARTICLE ANALYSIS USING DIAMOND MAGNETIC IMAGING that is incorporated by reference herein.

An applied magnetic field induces magnetization in bead A and an associated magnetic field from the bead. A magnetic field in the range of 0.5 to 10 mT, which may be generated with permanent magnets or an electromagnet, is sufficient to resolve features in the electron spin resonance spectrum of the diamond imaging sensor. The diamond magnetic imager images these bead fields directly, allowing for individual bead detection and location. Beads of similar composition and magnetization produce similar magnetic field patterns that may be identified as characteristic features 542 in a magnetic image corresponding to the location of each bead A. A representative image is shown in FIG. 6C.

Figure 6A:
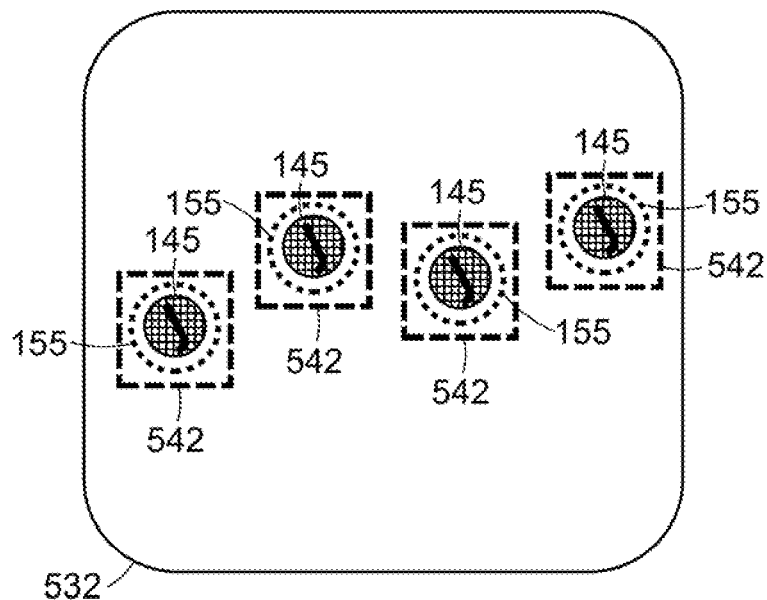
FIG. 6A schematically illustrates several complexes including magnetic beads and fluorescent beads in accordance with one or more embodiments.
Figure 6B:
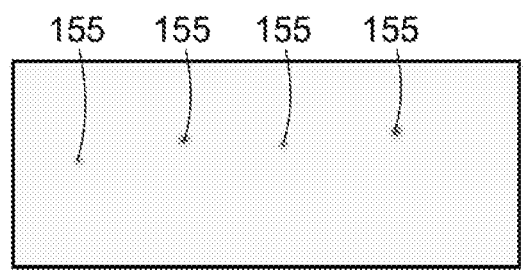
FIG. 6B illustrates a fluorescent image of the complexes shown in FIG. 6A in accordance with one or more embodiments.
Figure 6C:
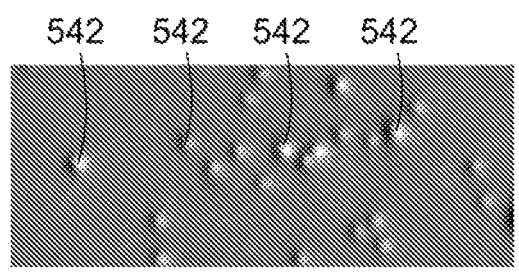
FIG. 6C illustrates a magnetic image of the complexes shown in FIG. 6A in accordance with one or more embodiments.

An image processing algorithm may identify the locations both of bead A features 542 in the magnetic image, shown in FIG. 6C, and bead B features 155 in the fluorescence image shown in FIG. 6B. Additional images may be acquired in either detection channel (magnetic or fluorescent) to improve signal fidelity. The resulting bead locations identified in each detection channel may then be compared to identify co-presence of both bead types, and hence of complexes 145 containing the target analyte, illustrated in FIG. 6A.

Adding the magnetic imaging channel to detect bead A in addition to detecting bead B in the bead fluorescence channel allows for identification of unbound bead B, which may persist after magnetic separation or which may dissociate from bead complexes that are weakly bound by nonspecific interactions. Unbound bead B may be rejected during analysis so that only bead B associated with complexes are counted.

Example D4: Fully Magnetic Assay with Magnetic Imaging

In another embodiment shown in FIGS. 7A-7D, bead A 710 and bead B 730 are both magnetic, but with distinguishable magnetic properties. Magnetic imaging with single-bead spatial resolution is used to identify bead A 710, as in Example C3, and also to identify bead B 730, distinguishing between the two. Bead A 710 has magnetic properties suitable for magnetic separation, as in Examples A1, B2, and C3 described above.

Beads A 710 and B 730 may, for example, differ in the shape and magnitude of their single-axis magnetization curves, which describe bead magnetization as a function of an applied magnetizing field. Beads A 710 and B 730 may differ in the degree of hysteresis in their magnetization curves and in properties such as remanent magnetization and coercivity. Beads A 710 and B 730 may have different degrees of asymmetry, with different magnetization curves observed when the field axis is changed. Beads A 710 and B 730 may respond differently to a time-varying magnetic field, such as an alternating or rotating field.

Using only magnetic imaging for identifying and locating bead A 710, bead B 730, and complexes 745 including the analyte 720 enables elimination of the optical fluorescence detection channel, simplifying the assay system significantly. Additionally, magnetic imaging is particularly insensitive to signal backgrounds due to unwanted light, detector noise, and sample contaminants that fluoresce, scatter, or absorb light. Magnetic signal backgrounds are extremely low in biological samples and they do not impede the ability to measure even modestly magnetic beads.

Distinguishing Magnetic Bead Types with Magnetic Imaging

Wide-field diamond magnetic imaging provides a means to directly image the vector magnetic field produced by a magnetic bead under a wide range of magnetic conditions. This general-purpose tool may be used to distinguish between magnetic bead types over a wide range of different properties.

In one embodiment, bead A 710 and bead B 730 are distinguished by measuring magnetic susceptibility and magnetic remanence at low applied field after first magnetizing the beads with a large magnetic field. Bead A 710 is superparamagnetic. For example, bead A 710 may be composed of superparamagnetic iron oxide nanoparticles 5-10 nm in size dispersed within a spherical polymer substrate approximately 1 μm in diameter. Bead A 710 may contain a quantity of iron oxide such that the magnitude of the average induced magnetization of bead A 710 with an applied bias field of 4 mT is approximately $3 \times 10^{-15}$ A m$^2$. Bead B 730 is ferromagnetic. In one embodiment, bead B 730 may be composed of ferromagnetic cobalt ferrite nanoparticles 30 nm in size dispersed over the surface of a spherical polymer substrate approximately 1 μm in diameter and adhered to the surface with an additional polymer layer. Bead B 730 has a remanent magnetization fraction of greater than 50%, such that, after being magnetized in a field of at least 300 mT and once the magnetizing field has been removed, bead B 730 retains a large proportion of its saturated magnetization value. Bead B 730 may contain a quantity of cobalt ferrite such that the magnitude of the average remanent magnetization of bead B 730 after the magnetizing field is removed is approximately $2 \times 10^{-15}$ A m$^2$.

A magnetic imaging procedure is described below for identifying complexes 745 containing the target analyte 720, bead A 710 and bead B 730.

Figure 7A:
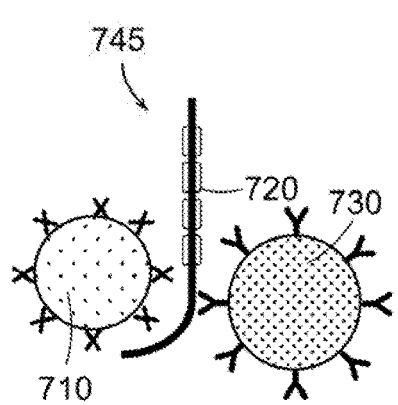
FIG. 7A schematically illustrates a complex that includes a magnetic functionalized bead of a first type, a magnetic functionalized bead of a second type, and an analyte in accordance with one or more embodiments.
Figure 7B:
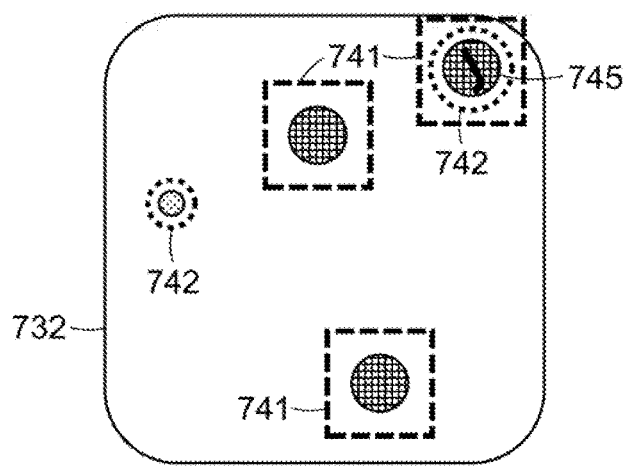
FIG. 7B schematically illustrates a complex including magnetic beads of the first and second types in accordance with one or more embodiments.

After forming complexes 745 in a sample suspension, a representative portion of the sample is disposed over and dried on the surface 732, shown in FIG. 7B, of a diamond magnetic imaging sensor shown in FIG. 5. The sensor's imaging surface is a {100} face and this surface contains a thin layer approximately 1-μm thick that is rich in nitrogen-vacancy (NV) centers. Turning back to FIGS. 7B-7D, after magnetic imaging, complexes 745 are identified by identifying bead A 710 and bead B 730 in close proximity to one another, including close enough to be spatially unresolved in the images. Prior to magnetic imaging, a magnetizing field is applied in a direction normal to the horizontal diamond surface. A field of greater than 200 mT applied for a period of several seconds is sufficient to magnetize the magnetic material in bead B. The dried sample is then magnetically imaged twice with a bias magnetic field of 4 mT applied parallel to one crystal axis of the diamond sensor, which is oriented at an angle of approximately 35 degrees with respect to the imaging surface. The 4 mT imaging field is reversed between acquiring the two magnetic images, shown in FIGS. 7C and 7D, termed the positive (FIG. 7C) and negative (FIG. 7D) images, denoting the +4 mT and −4 mT imaging fields, respectively. The magnetic images measure the projection of the sample magnetic field vector onto the axis of the imaging field.

Since bead A 710 is superparamagnetic, the greater than 200 mT magnetizing field does not leave bead A 710 with significant remanent magnetization. In both the positive and negative images, the magnetization of bead A is only that which is induced in the superparamagnetic beads by the 4 mT imaging field. Bead A 710 produces the same feature 741 in both magnetic images, since the bead A 710 magnetization is in both cases parallel to the imaging field.

Figure 7C:
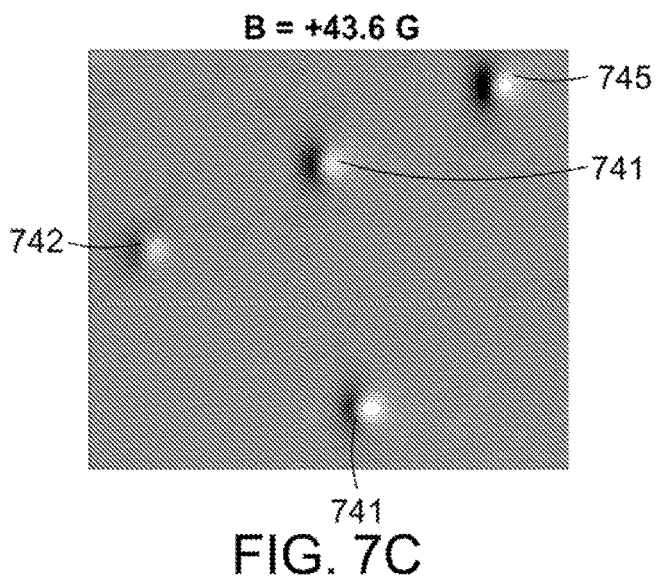
FIG. 7C illustrates a positive magnetic image of the magnetic beads shown in FIG. 7B in accordance with one or more embodiments.
Figure 7D:
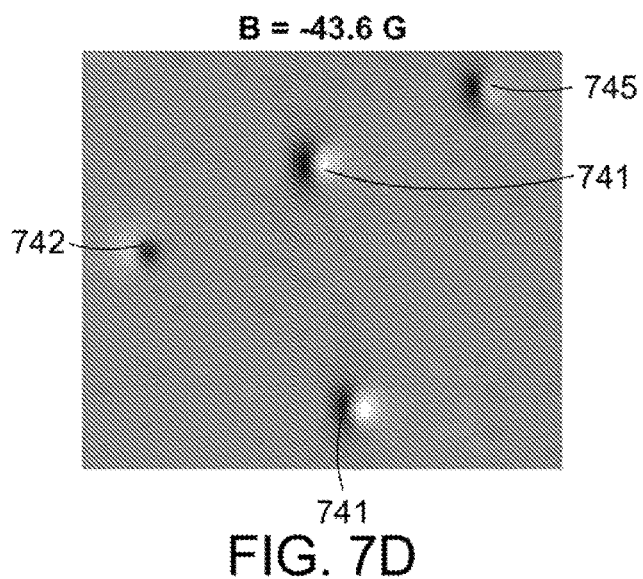
FIG. 7D illustrates a negative magnetic image of the magnetic beads shown in FIG. 7B in accordance with one or more embodiments.

In contrast, the greater than 200 mT magnetizing field leaves bead B 730 strongly magnetized in the vertical direction, oriented up with respect to the horizontal diamond sensor imaging surface. Once the magnetizing field is removed, the weaker 4 mT imaging field does not significantly change the magnetization of bead B 730, since the magnetic susceptibility of bead B 730 near zero magnetic field, when previously magnetized along the same axis, is low. Therefore, bead B 730 produces an image feature 742 that inverts sign between the positive and negative magnetic images, with positive magnetic field projection changing to negative and vice versa, as illustrated in FIGS. 7B, 7C, and 7D.

All magnetic objects identified in the magnetic image field of view are quantified by magnetization, such that bead A 710 is assigned a positive value in both images and bead B 730 is assigned a positive and negative value in the positive and negative images, respectively. Bead complexes 745 will be assigned magnetization values that reflect the complex composition. For example, bead dimers of the form A-A or B-B will generally be assigned larger values with the same sign of bead A or bead B monomers, respectively. Bead dimers 745 of the form A-B or larger heterogeneous bead complexes will be assigned values of smaller magnitude in the negative image than in the positive image, reflecting oppositely-magnetized beads within the complex, as shown in FIGS. 7C and 7D.

Figure 8A:
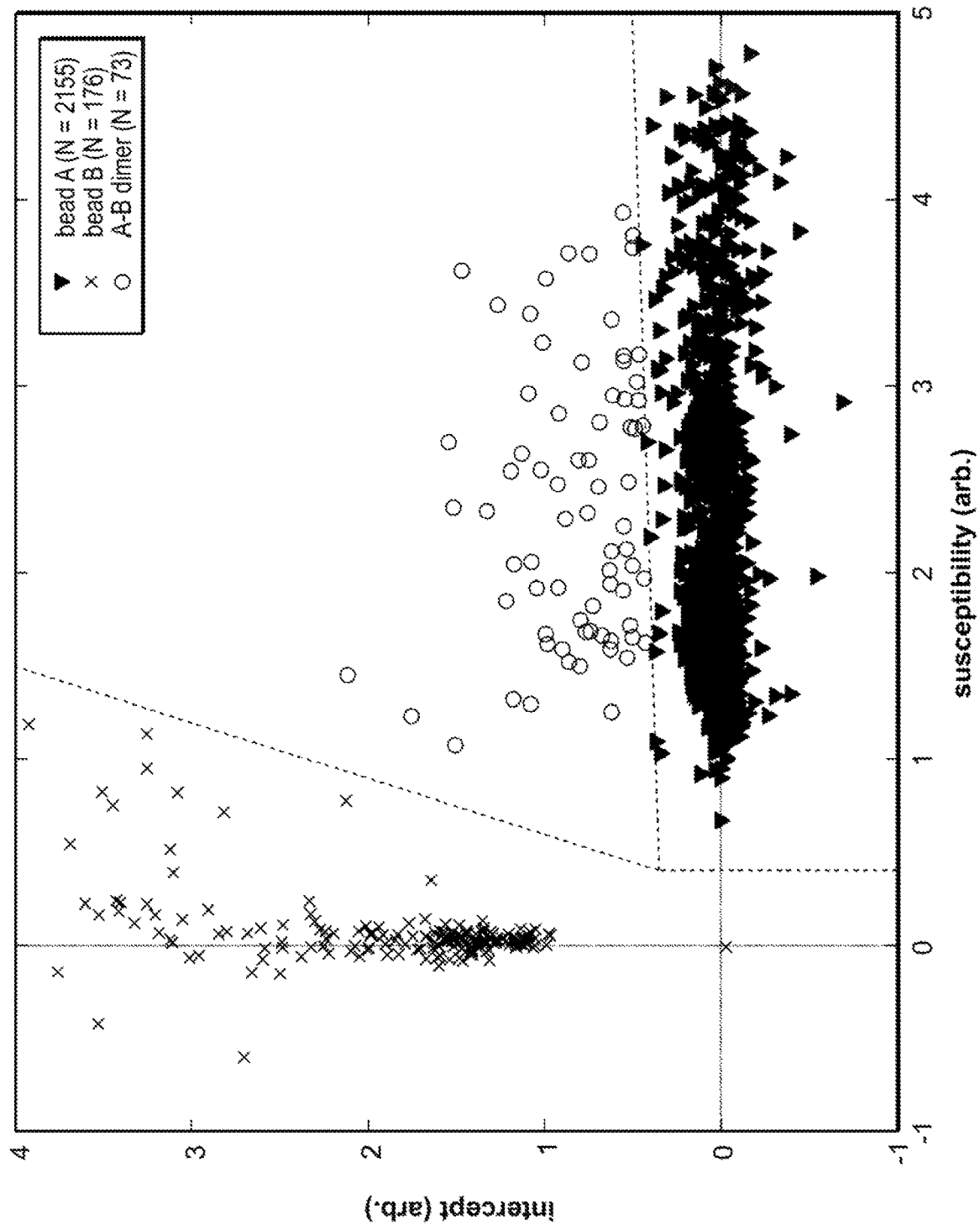
FIG. 8A illustrates magnetic bead discrimination based on remanence and susceptibility in accordance with one or more embodiments.

All magnetic objects in the magnetic images may be represented on a scatter plot whose axes are the sum and difference, respectively, of the positive and negative image magnetization values. This sum and difference may also be termed the susceptibility and remanence of the single-bead magnetization curve, as they are approximately proportional to these properties. As shown in FIG. 8A, bead A and bead complexes containing only bead A will be clustered near one axis, with large susceptibility and zero remanence; bead B and bead complexes containing only bead B will be clustered near the other axis, with large remanence and near-zero susceptibility. Complexes containing both bead A and bead B will exhibit significant susceptibility and remanence, so they may be identified as the objects in the scatter plot in a region sufficiently separated from both axes. This region is unlikely to contain signals from bead A or bead B alone, or from homogeneous bead complexes such as those of the form A-A or B-B.

If the magnetic imaging spatial resolution is sufficient to resolve individual magnetic beads within a complex, then the complex may be identified by separately identifying beads within the complex and determining their spatial separation to be consistent with that of a bound complex, and not significantly greater than the bead diameters.

If both bead A and bead B are sufficiently magnetic, and either bead A or bead B is ferromagnetic, A-B dimers may form even in the absence of the target analyte, due to attractive magnetic interactions. These magnetic interactions may be limited in strength by limiting the amount of magnetic material in each bead. Magnetic bead signals may be measured even in cases in which magnetic interactions between beads are too weak to overcome forces associated with Brownian motion or sample mixing, so that magnetic interactions may play no role.

The magnetic material within bead A and bead B may be composed of nanoparticles disposed within or on the surface of a polymer or other nonmagnetic substrate. If the nanoparticles are uniformly disposed within or on the surface of the substrate, then the strength of magnetic interactions between beads can be reduced relative to having aggregated nanoparticles, since magnetic fields near aggregated magnetic nanoparticles may be stronger. Using nanoparticles that are much smaller than the substrate radius may allow for more uniform distribution, relative to larger nanoparticles that produce stronger local magnetic fields.

Magnetic interactions may also be suppressed by adding a nonmagnetic layer encapsulating the magnetic material. Suitable materials for the nonmagnetic layer include polymers, such as polyethylene (PE), polytetrafluoroethylene (PTFE), and polymethylmethacrylate (PMMA). Since magnetic interactions weaken rapidly with increasing separation between beads, even a nonmagnetic layer significantly thinner than the original bead radius can dramatically reduce dimer formation due to magnetic interactions.

Additional Magnetic Discrimination Methods
Discrimination by Magnetic Moment

Figure 8B:
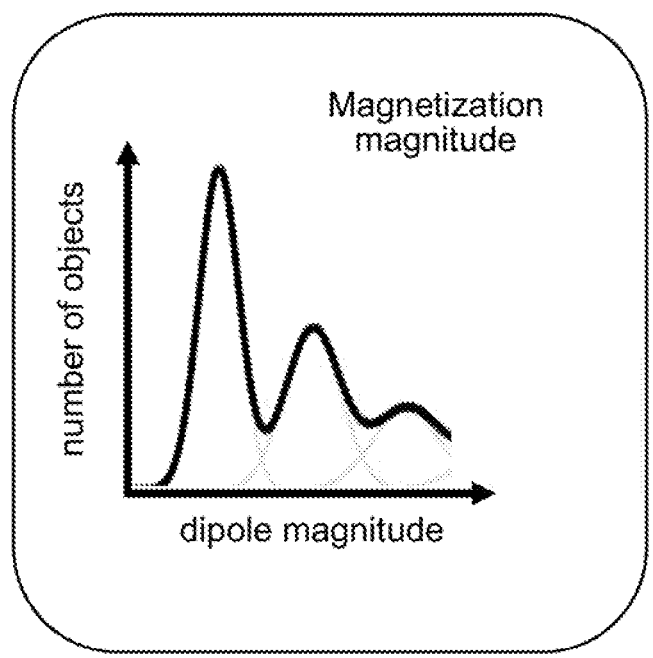
FIG. 8B illustrates magnetic bead discrimination based on magnetization magnitude in accordance with one or more embodiments.

As shown in FIG. 8B, the magnetic image signal for a magnetic bead can be analyzed to determine the magnetic moment (magnetization×volume) of the bead, assuming knowledge of the bead size and a spherically symmetric distribution of magnetic material in the bead. For bead A and bead B of similar size, the magnetic moment can be used to distinguish between bead A, bead B, and bead complexes. To be effective, there must be low enough variation of magnetic moment, size, and spherical symmetry of each bead such that each measurement can be clearly associated with one distribution. The A-B complex, having larger size than each individual bead, may not produce a signal equal to the sum of signals from bead A and bead B. Nevertheless, the bead A and bead B magnetic moments may still be chosen such that the mean A-B complex signal is distinct from that of bead A, bead B, the A-A complex, the B-B complex, etc. It is not necessary to resolve spatial differences between candidate signals to discriminate them by magnetic moment; it is sufficient to evaluate each signal only by magnitude, e.g. magnitude of convolution with a characteristic image signal.

If bead A and B have different size, a similar discrimination approach may be used that ignores this size difference when evaluating the magnitude of candidate signals and applies the same single-parameter quantification strategy to all signals. This may produce signals for bead A, bead B and complexes that are not proportional to their magnetic moments, but are distinct and allow for accurate discrimination.

Discrimination by Anisotropy

Magnetic particles may exhibit an anisotropic response to a magnetic field, due to preferential magnetization along certain crystal axes in a single magnetic domain or along certain directions in a multi-domain particle or a composite magnetic bead containing many particles. Rod-shaped nanoparticles, for example, typically can be magnetized more easily along the rod axis. Synthesizing a spherical bead containing oriented magnetic nanorods would produce an anisotropic magnetic susceptibility in the bead.

Figure 8C:
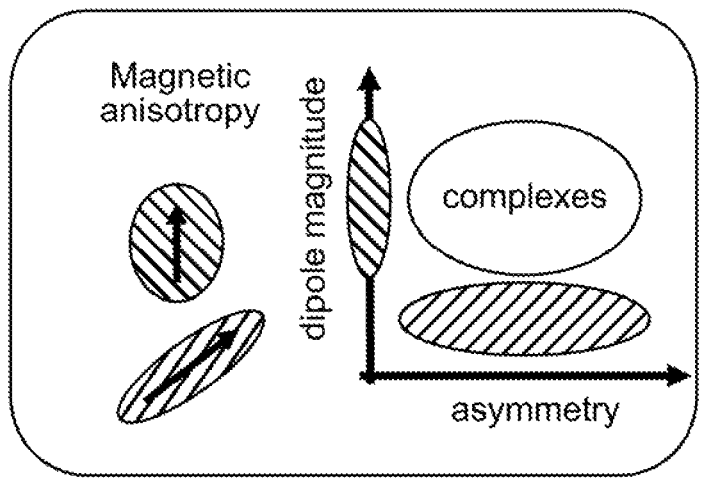
FIG. 8C illustrates magnetic bead discrimination based on magnetic anisotropy in accordance with one or more embodiments.

The magnetic anisotropy of a bead can be probed by imaging immobilized beads multiple times, using multiple directions of an applied magnetic field. As shown in FIG. 8C, a metric for magnetic anisotropy can be constructed from the difference in magnetic signals obtained from the different orientations. Imaging at three distinct directions is sufficient to determine the orientation and degree of anisotropy for a particle even if the particle orientation is not known in advance. If bead A and bead B have zero and nonzero magnetic anisotropy, respectively, then images acquired with the imaging magnetic field rotated in different directions will produce identical signals for bead A, but different signals for bead B. Complex signals will have nonzero anisotropy, but less than that of bead B.

Discrimination by Coercivity

Figures 8D, 8E, 8F:
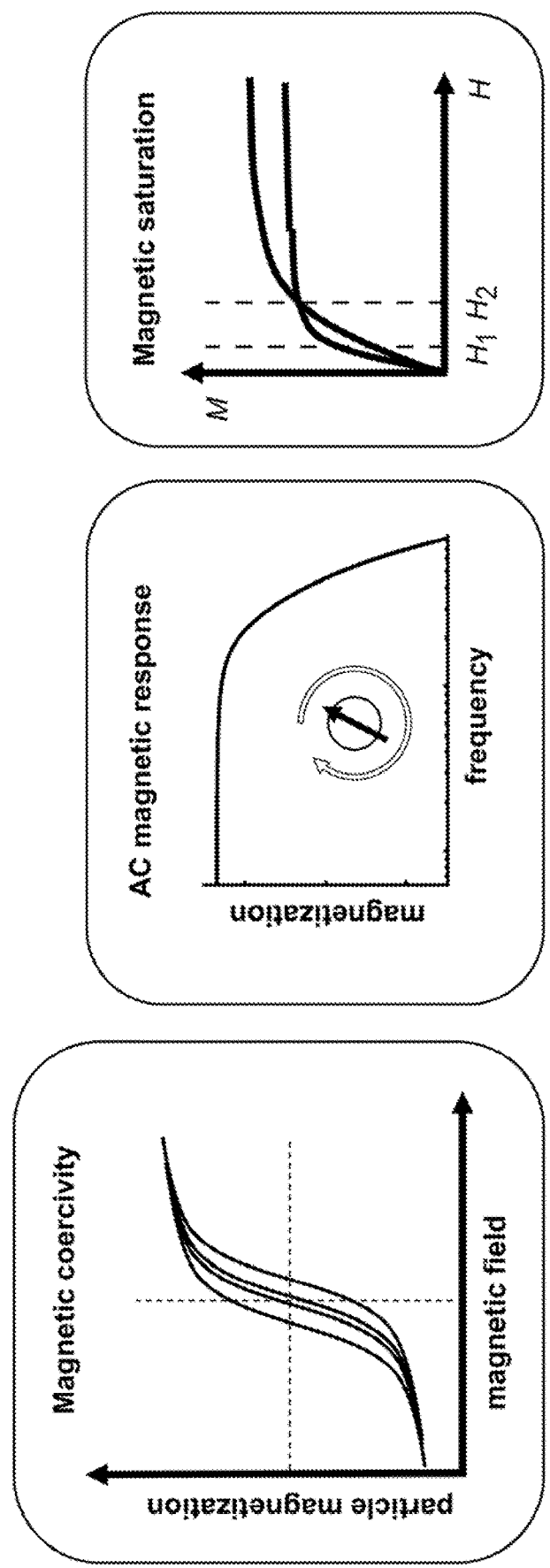
FIG. 8D illustrates magnetic bead discrimination based on magnetic coercivity in accordance with one or more embodiments.
FIG. 8E illustrates magnetic bead discrimination based on AC magnetic response in accordance with one or more embodiments.
FIG. 8F illustrates magnetic bead discrimination based on magnetic saturation in accordance with one or more embodiments.

As shown in FIG. 8D, magnetized ferromagnetic beads can be re-magnetized in a different direction by applying a field larger than the coercivity. Discrimination between two types of ferromagnetic beads, bead A and bead B, can be achieved using this sequence: (1) first magnetize both beads with a strong magnetic field in one direction; (2) image the bead magnetization; (3) apply a magnetic field in the opposite direction that is strong enough to reverse the magnetization of bead A, but not strong enough to reverse the magnetization of bead B; (4) image the magnetic bead signals and compare them to those in the first image. Bead A signals will reverse direction; bead B signals will change modestly, if at all; complex signals will change significantly in magnitude as one bead in the complex reverses magnetization while the other does not.

Discrimination by time-dependent magnetic response

As shown in FIG. 8E, magnetic particles change their magnetization direction in response to a change in magnetic field direction. For a given field strength, the time scale for a particle to change direction may depend on the particle composition and size and may vary over a wide range from below 1 µs to well over 1 s. If an oscillating or rotating AC magnetic field of constant amplitude is applied to the particle, the particle magnetization will oscillate in response. An oscillating magnetization may be measured by a magnetic imaging technology that is sensitive to AC magnetic fields, such as a wide-field ODMR center magnetic imaging system that employs pulsed optical excitation of ODMR centers or time-gated camera exposures. The magnitude of the oscillating magnetization will decrease as the oscillation period decreases below the time scale required for the particle to change magnetization direction. The cutoff frequency is defined as the oscillation frequency corresponding to this change in response.

If bead A and bead B contain magnetic material with different cutoff frequencies, measuring the oscillating magnetization at multiple oscillation frequencies provides a method to discriminate between the beads. If bead A has a high cutoff frequency compared to bead B, then imaging at an intermediate frequency will observe a weak bead B signal compared to imaging at a low frequency, but little change in the bead A signal. A complex will exhibit a decrease in signal at the intermediate frequency that is smaller than that of bead B. Discrimination can be improved by adding additional images at additional frequencies. While bead A and bead B will have a single cutoff frequency, the complex will exhibit two cutoff frequencies. Signals obtained at low oscillation frequency and at two or more intermediate frequencies will reveal qualitatively different behavior for bead A, bead B, and complexes.

Discrimination by Magnetic Saturation

As shown in FIG. 8F, the magnetization M of a superparamagnetic particle saturates with sufficiently high magnetic field H. Even at field strengths below saturation, the magnetic susceptibility (slope of the magnetization curve) is reduced. If the magnetizations of superparamagnetic bead A and bead B saturate at different field strengths $H_1$ and $H_2$, then the beads may be distinguished by imaging at two magnetic field strengths, one of which is large enough to observe a change in magnetic susceptibility in one of the beads. The ratio of signals in these two images will be significantly different for bead A and bead B. Complexes will have an intermediate ratio distinct from that of bead A or bead B.

Size Based Magnetic Bead Discrimination

Magnetic beads of different size, but similar composition, may produce magnetic image signals that are distinguishable by their spatial scale. This may allow for discrimination between bead A, bead B, and complexes, despite bead A and bead B having nominally identical magnetic properties.

When the sample solution is disposed on a surface, most beads will come to rest against the surface, so that the center of each bead is spaced from the surface by its radius. Larger beads are thus centered further from the sensing surface than smaller beads. This spacing determines the spatial scale of the magnetic field at the sensing surface, since the same lateral displacements along the surface are relatively larger for closely-spaced beads than for more distant beads, and therefore result in larger relative changes in magnetic field.

Figure 9:
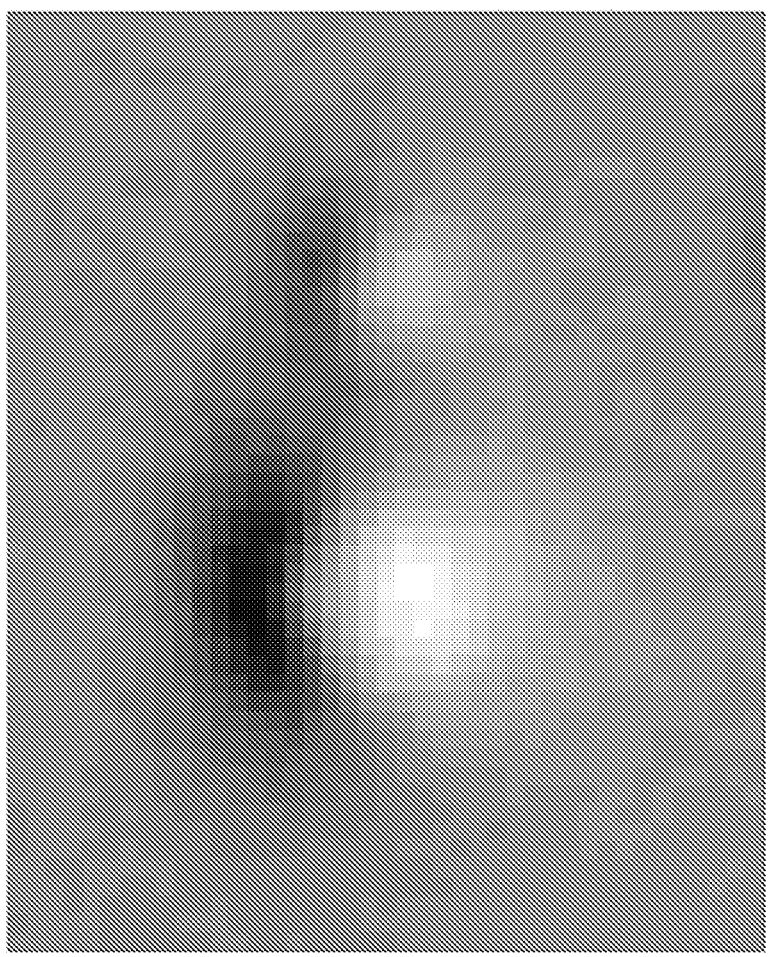
FIG. 9 illustrates a magnetic image of two beads of different sizes in accordance with one or more embodiments.
Figures 1, 10C:
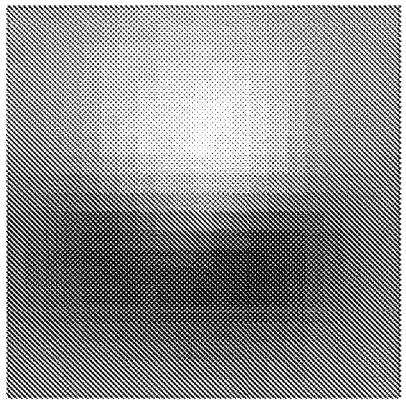
FIGS. 10A-1, 10B-1, and 10C-1 illustrate magnetic images of the image signal of three beads B in accordance with one or more embodiments.
Figures 2, 10C:
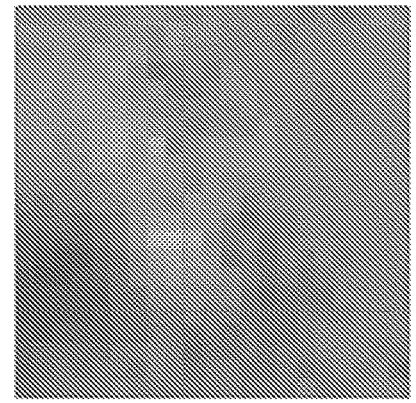
Figures 1, 10B:
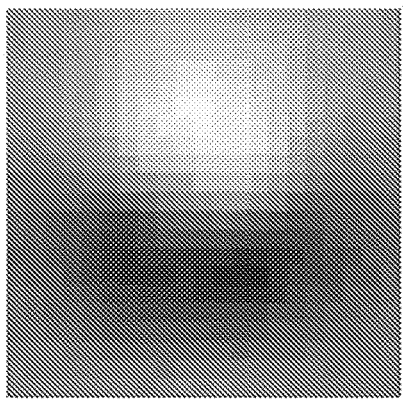
Figures 2, 10B:
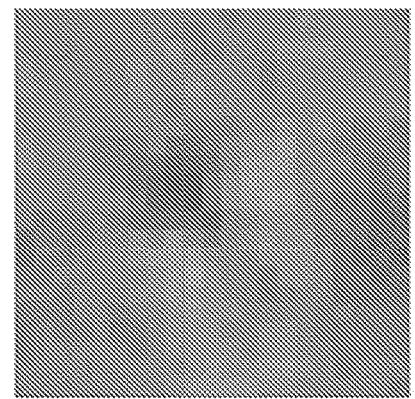
Figures 1, 10A:
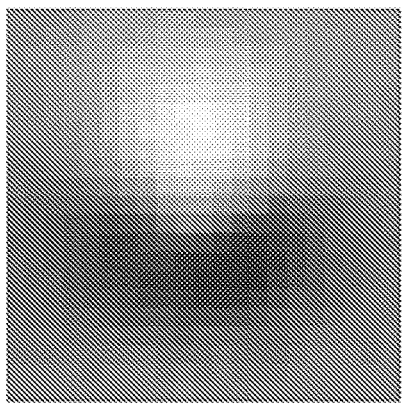
Figures 2, 10A:
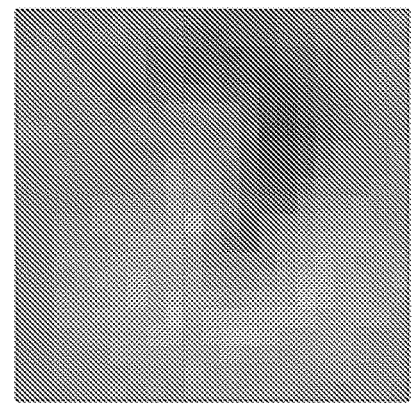

FIG. 9 is an image of two beads, approximately 1 micron (top) and 3 microns (bottom) in diameter, with their centers spaced approximately 9 microns apart. The larger bead produces a magnetic signal with broader spatial features. In this case, the larger bead also contains more magnetic material and produces a larger magnitude of signal, but this need not be the case.

If bead A and bead B have different size, but similar magnetic properties, then spatial scale of magnetic image signals may be used not only to discriminate between the two, but also to identify A-B complexes. Complexes have spatially broad signals that also contain shorter-scale spatial components.

One method for identifying complexes is to first identify all broad signals (including both bead B and complex signals) and then subtract a characteristic bead B signal (such as the mean of many bead B signals imaged separately) from each. Variations in imaging accuracy and in the uniformity of bead B magnetization will cause this difference to be nonzero for bead B signals, however the difference will generally have broad spatial scale. For the complex signals, however, subtracting the characteristic bead B signal will leave behind the sharper bead A signal. These cases may be distinguished by spatial filtering of the signal differences.

FIGS. 10A-1, 10B-1, and 10C-1 show example bead B images. The difference signal images after subtracting the characteristic bead B signal shown in 10A-2, 10B-2, and 10C-2 have a gray scale amplified by a factor of 2.

FIGS. 11A-1, 11B-1, and 11C-1 show example complex images, showing sharp bead A signals circled in the difference images shown in 11A-2, 11B-2, and 11C-2, which are again amplified by a factor of 2 relative to the image signals.

Combined Approaches

The bead discrimination approaches described herein may also be used in combination to enhance discrimination performance or to discriminate between more than two bead types and their combinations.

Additional Assay Features

Accounting for Variation in Bead Density

For a given number of bead complexes containing the target analyte in a liquid sample suspension, the number of complexes present within an imaging field of view after disposing the sample over the imaging sensor may vary due to differences in the manner in which the sample was disposed. For example, the sample may be disposed over the sensor by adding a liquid droplet to the sensor surface and allowing it to dry, such that variations in the droplet volume or its initial contact area with the sensor lead to variations in bead complex density in the dried sample over the sensor surface. By measuring the total number of bead A in the field of view, including the unbound beads not contained in complexes, the sample density variations may be measured and accounted for. Dividing the number of complexes by the number of bead A yields a quantity that is less sensitive to variations in sample density, and thus may provide a more precise measurement of the total number of bead complexes in the sample and of the analyte concentration determined from a calibration curve obtained as described above.

Accelerated Bead Interaction Kinetics

It is known in the art that immunoassays must allow time for target analytes in a liquid sample to bind to antibodies that enable detection of the target analytes. Depending on the reagent concentration and sample conditions (such as temperature, viscosity, and process for agitating or mixing the sample), several minutes may be required for most analytes to become bound, even when there is a large excess of binding sites available, due to the time needed for the analyte to move through the sample by diffusion or active shaking or stirring.

The rate of interactions between different beads in the sample suspension may determine multi-bead assay speed, since bead diffusion is generally slower than diffusion of smaller molecular analytes. Since a bead-bound target analyte may also occupy a relatively small fraction of the bead's surface area, when the bead to which the analyte is bound interacts with a second bead, the analyte may not be exposed to the second bead in a manner conducive for binding (e.g., the interaction occurs on the side of the first bead opposite to where the analyte is located). Several bead interactions may be required on average to form an immunocomplex. The multi-bead assay time may be shortened by performing processes to induce bead-bead interactions that lead to immunocomplex formation, accelerating bead kinetics beyond what may be expected for diffusion or stirring alone.

In one embodiment, bead-bead interactions may be induced by agglomerating a plurality of functionalized beads of the first and second types, after contacting the sample solution with the population of functionalized beads of the second type, before detecting the complex, by means of spinning the sample suspension on a centrifuge to concentrate the beads into a pellet in the sample tube. This process can be performed in less than a minute with standard benchtop centrifuge systems. Beads in the pellet may be closely spaced or in contact with one another, resulting in many bead interactions in the pellet. The pellet may be re-suspended by mixing the suspension. This centrifuge process may be repeated as necessary to ensure sufficient interactions between beads to form immunocomplexes containing the target analyte.

In another embodiment, if both bead A and bead B are magnetic, then magnetic separation may be used to form a pellet of beads in the sample suspension and induce bead-bead interactions by applying a magnetic field gradient to the sample solution after contacting the sample solution with the functionalized beads of the first and second types. As with the centrifuge process, this magnetic approach to accelerating bead kinetics can be performed in less than a minute and repeated as necessary to form immunocomplexes containing the target analyte. The magnetic approach may be performed with permanent magnets for a simple, inexpensive, and compact process with minimal power consumption. An electromagnet may also be used to apply the magnetic field with no moving parts.

In another embodiment, a bead pellet produced by magnetic separation of a sample suspension can be agitated without removing the magnetic field, but by varying or otherwise changing the magnetic field gradient applied to the sample solution with respect to the beads. For example, the field magnitude, direction, or spatial distribution may be changed or oscillated to apply different magnetic forces on the beads. Alternatively, or additionally, the sample tube may be moved with respect to the magnetic field. For example, rotating the tube may move the pellet away from its equilibrium position so that the pellet will be dragged by the magnetic field gradient to a new position. These changes will cause beads in the pellet to move with respect to each other and may induce additional bead interactions and immunocomplex formation.

In an embodiment, a permanent magnet may be moved relative to a tube containing a sample suspension with magnetic beads of multiple types. The magnet may follow a fixed pattern of motion. Exemplary cases include the magnet orbiting the sample tube in a circle, rotating on its own axis, or rocking back and forth between two points. The motion may be continuous, in which case the bead pellet will continuously move through the tube, subjecting the beads to shear forces from the liquid, tube walls, and other beads. This motion and the associated forces on the beads will agitate the pellet continuously to drive bead-bead interactions. In another exemplary case, the motion may occur in discrete periods separated by periods of rest, in which the bead pellet may concentrate to a higher bead density than is achieved during continuous motion. If the different bead types respond significantly differently to the field of the permanent magnet, then the periods of rest will allow the multiple bead types to co-localize more effectively than during continuous motion.

In another embodiment, a plurality of permanent magnets may be moved relative to a plurality of samples in separate wells of a plate, such that the sample in each well is subjected to a magnetic field profile in time and space that is substantially similar. This approach allows for driving bead-bead interactions in parallel over a plurality of samples for improved sample preparation throughput.

Accelerating bead kinetics and the rate of bead-bead interactions in sample suspension decreases the time required to bind target analytes into detectable multi-bead complexes. This method enables a rapid assay.

This method may also allow for a lower quantity of binding ligands to be used on the bead surfaces, since the likelihood of a given ligand to bind to the target analyte may be increased by the increased frequency of bead-bead interactions. Using fewer binding ligands may reduce the cost of the assay significantly.

Multiplexing

It is often useful for an assay to measure concentration of multiple distinct analytes in a single sample. A multiplexed assay measures distinct target analytes by associating a distinct signal with each target, so that the analyte signals may be distinguished in the assay measurement. The magnetic dual-bead assay may be generalized to a multiplexed multi-bead assay by using more than two distinguishable bead types. Different analytes may be specifically detected by observing the formation of analyte-specific complexes including a plurality of functionalized beads of at least a third type, functionalized to include at least a third moiety that can specifically associate with at least a second analyte under appropriate conditions.

Figure 12B:
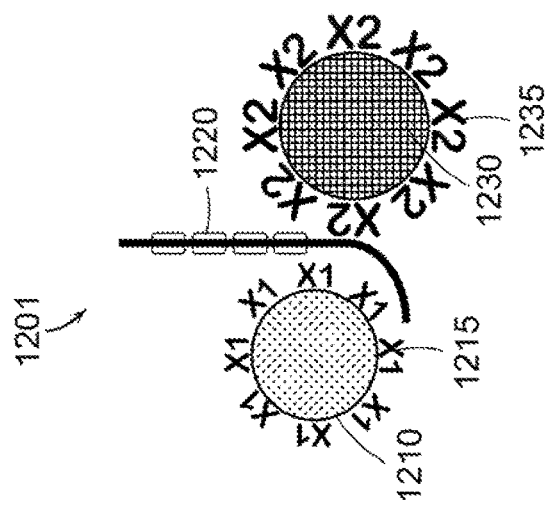
FIG. 12B schematically illustrates complexes including four distinguishable bead types in accordance with one or more embodiments.
Figure 12B:
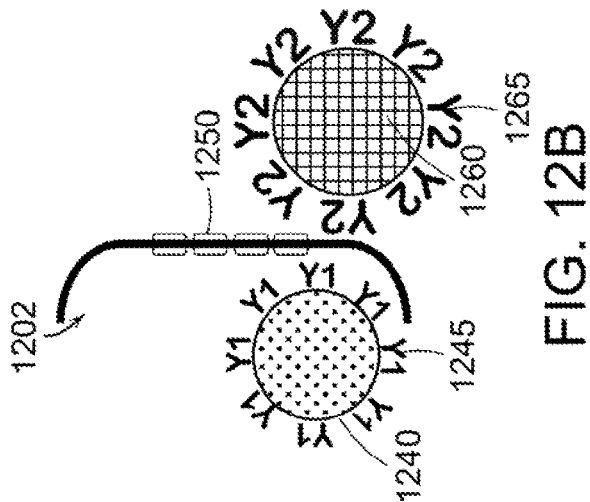
Figure 12A:
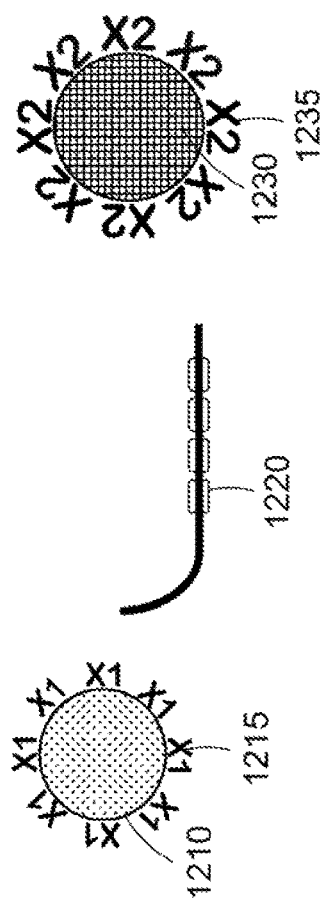
FIG. 12A schematically illustrates a multiplexed assay including four distinguishable bead types in accordance with one or more embodiments.
Figure 12A:
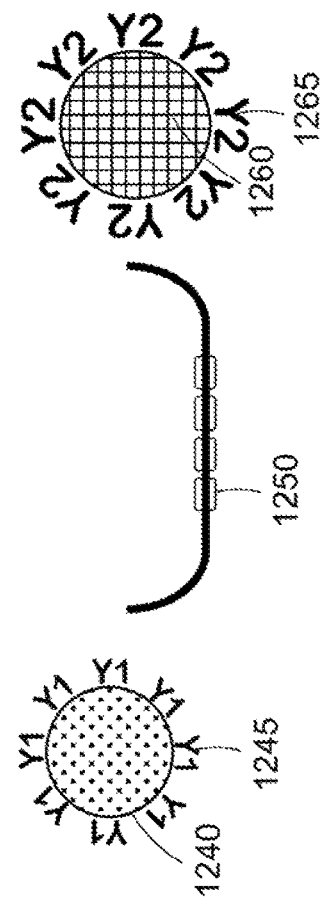

In one embodiment, shown in FIGS. 12A and 12B, consider a plurality of functionalized beads of the third type 1240 functionalized to include at least a third moiety 1245 that associates with the second analyte 1250 under suitable conditions, and a plurality of functionalized beads of a fourth type 1260, functionalized to include a fourth moiety 1265 that associates with the second analyte 1250 under suitable conditions, resulting in four distinguishable bead types: bead A 1210, bead B 1230, bead C 1240, and bead D 1260. Complexes of the form A-B 1201 or C-D 1202 may be formed through binding of two distinct analytes, first analyte X 1220 and second analyte Y 1250, to moieties coating each bead. In this case, bead A 1210 and bead B 1230 are coated with moieties 1215 and 1235, respectively, targeting two distinct regions X1 and X2 of analyte X 1220; bead C 1240 and bead D 1260 are coated with moieties 1245 and 1265, respectively, targeting two distinct regions Y1 and Y2 of analyte Y 1250. The moieties on each bead are unique to that bead. The A-B 1201 and C-D 1202 complexes may be distinguished from each other and from the monomer beads from their distinct magnetic properties.

Figure 13A:
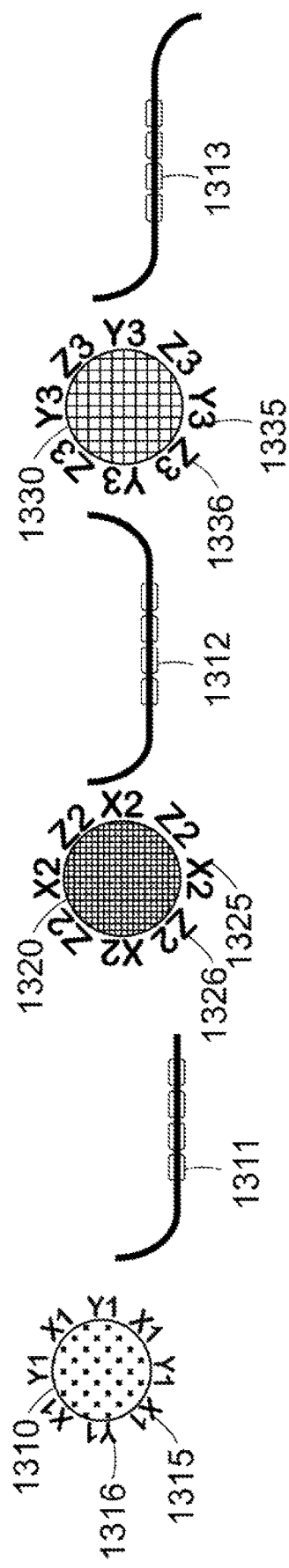
FIG. 13A schematically illustrates a multiplexed assay including three distinguishable bead types in accordance with one or more embodiments.
Figure 13B:
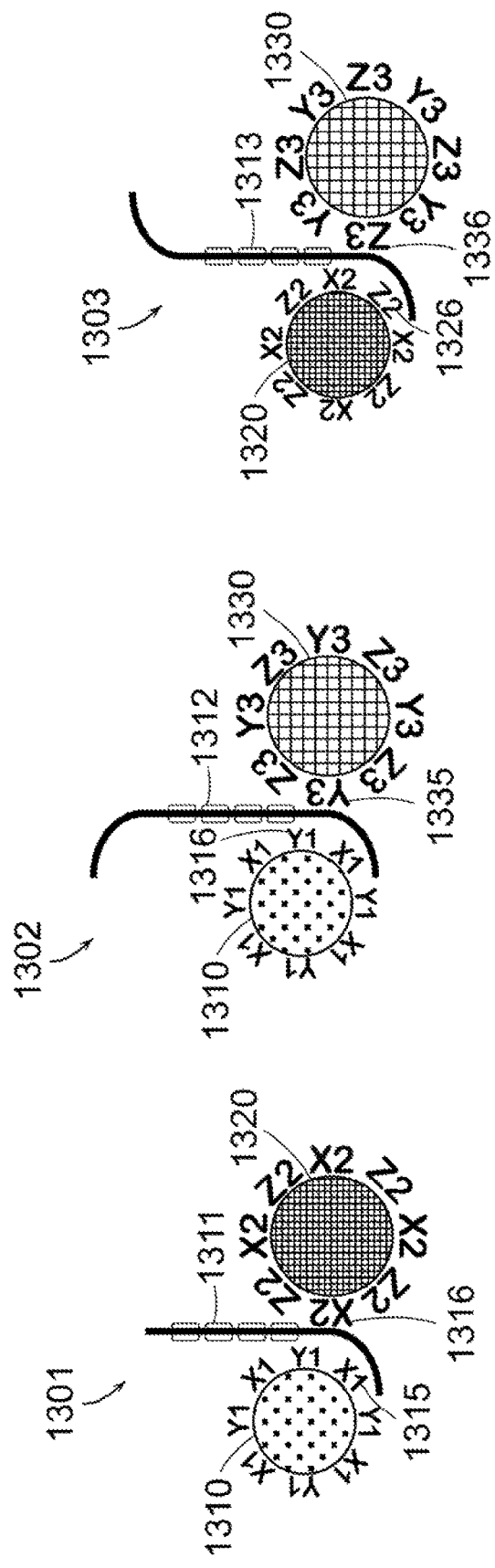
FIG. 13B schematically illustrates complexes including three distinguishable bead types in accordance with one or more embodiments.

In another embodiment, shown in FIGS. 13A and 13B, consider three distinguishable bead types: bead A 1310, bead B 1320, and bead C 1330. Complexes of the form A-B 1301, B-C 1302, or A-C 1303 may be formed through binding of three distinct analytes, analyte X 1311, analyte Y 1312, and analyte Z 1313, to moieties coating each bead. The functionalized beads of the first type A 1310 further include at least one additional moiety 1316 that associates with the second analyte 1312 under suitable conditions. The functionalized beads of the second type B 1320 further include a moiety 1326 that associates with the third analyte Z 1313 under suitable conditions. The functionalized beads of the third type C 1330 are functionalized to include a moiety 1335 and a moiety 1336, and therefore each bead is coated with two distinct moiety types targeting two different analytes: bead A 1310 is coated with moieties for analyte X 1315 and for analyte Y 1316; bead B 1320 is coated with moieties for analyte X 1325 and for analyte Z 1326; bead C 1330 is coated with moieties for analyte Y 1335 and for analyte Z 1336. The moieties on each bead are unique to that bead. The A-B 1301, B-C 1302, and A-C 1303 complexes may be distinguished from each other and from the monomer beads from their distinct magnetic properties.

Multiplexed assays must have a means of discriminating between signals associated with distinct target analytes, which in the case of multiplexed bead assays means that the beads must be distinguishable. Bead fluorescence may be used to discriminate between bead types with different excitation and/or emission spectra. For example, three bead types may emit blue, yellow, or red fluorescence that may be distinguished using optical filters. Different bead types may also be prepared to fluoresce with different intensities, so that the different types may be distinguished in a fluorescence image by discrete levels of brightness, where difference between the levels exceeds variation within the distribution of each bead type.

Distinct magnetic bead types may be distinguished by preparing bead types with different magnetic properties that can be distinguished by magnetic imaging. In an exemplary case, the distinct bead types may be prepared by loading each bead type with specific and distinguishable quantities of magnetic material. In another exemplary case, distinct bead types may be prepared by loading each bead type with different magnetic material exhibiting different properties. The fully magnetic multi-bead assay described above discriminates between two bead types in this manner. A multiplexed assay may be implemented by adding additional distinguishable beads using distinct combinations of the properties described above. For example, bead A may be superparamagnetic, while bead B and C are ferromagnetic with different coercivities derived from bead B and bead C comprising different ferromagnetic materials. In this case, the beads may be distinguished by measuring magnetic remanence after magnetization, and then also measuring whether this remanence is reversed upon application of a demagnetizing field that exceeds the coercivity of bead B, but not that of bead C. The three beads in this case may be used to implement a multiplexed assay for three analytes using an embodiment described above.

Sample Preparation

One example of suitable conditions for sample preparation for the multi-bead assay is to combine a few drops of blood with the multi-bead mixture, incubate for a few minutes with accelerated kinetic mixing and deposit the sample solution on the diamond surface to dry followed by magnetic imaging. The sample solution can be partially or completely dehydrated before detecting the complex.

A suitable sample preparation proceeds as follows: plasma or serum is diluted in assay buffer 10-fold by adding 5 µL sample into 45 µL assay buffer and briefly vortex mixed. This diluted sample is further diluted 2× with 50 µL of bead mix for a final of 100 µL. The bead mix includes ~100,000 capture beads and ~100,000 detector beads. The final assay reaction is 20-fold dilution of sample in 100 µL. The assay reaction is incubated with vortex mixing (800 rpm) for 15 minutes at room temperature. The samples are then placed in a centrifuge and spun at 1500 g for 3 minutes, followed by pulse vortex mixing. The centrifugation and mixing cycle is repeated twice more, after which the sample is placed against a permanent magnet (magnetic field ~300 mT) for 30 seconds to pellet the magnetic beads against the sidewall of the reaction tube. The assay volume is removed by pipette leaving the bead pellet intact on the side wall against the magnet. The tube is removed from the magnet and the pellet is suspended in 500 µL of wash buffer by vortex mixing. The tube is pulse spun at 1500 g for 3 seconds to remove fluid from the cap, and placed on the magnet for 30 seconds. The wash cycle is repeated 2 more times for a total of 3 washes. The pellet is washed 1 time with 200 µL of imaging buffer and finally suspended in ~4 µL imaging buffer. ~2 µL is applied to the diamond sensor for magnetic imaging.

The sample may be any chemical or biological sample, such as whole blood, blood components (plasma, serum), tissue culture, cell culture, bodily fluids (cerebral spinal fluid (CSF), tears, saliva, breast milk, urine, semen, nasal discharge), tissue samples (oral swabs, biopsies, surgical resections), recombinant DNA, RNA or protein, endogenous DNA, RNA or protein, synthetic nucleic acids or protein peptides.

Further sample requirements may include volumes of sample types from 0.1 µL to 1000 µL.

Further sample requirements may include dilution of sample types and volume into assay buffers. Dilutions of sample types may include dilution by a factor of 10-1,000. Assay buffers may be determined empirically for optimized signal generation and minimized non-specific background, or false binding of any kind.

Samples may be combined in various ways including, for example, with multi-bead mixtures in blood collection tubes, assay tubes, assay plates/well, microfluidic devices, reaction chambers, incubation chambers, lateral flow devices, blood component separation devices, or other liquid handling or manipulation devices.

Samples may be mixed in various ways including, for example, by magnetic fields, centrifugal force, gravity, sound induced, light induced, electric induced, ionic interactions, van der Waals induced, Brownian motion, spinning, or other mechanical means.

Samples may be mixed with multi-bead mixtures for times necessary to capture targets of interest ranging from, for example, a second to several hours.

Samples may be introduced to the magnetic imaging device in various ways including, for example, by pipette, capillary flow tube or device, sample handling device, liquid handling device, integrated device, lateral flow device, disposable or reusable device.

Samples may be deposited on the diamond surface by several modes of application including, for example, pipetting, pouring, dripping, capillary flow, pumping, gravity induced flow, magnetic induced flow, ionic induced flow, sound induced flow, light induced flow, mechanical vibration induced flow, sheath flow, centrifuge induced, and thermal induced flow.

Samples may be magnetically imaged in a dry, dehydrated (i.e., partially dry or gel), or wet state.

Further Example Embodiments

Example 1 is a bead-based magnetic assay system for detecting a complex including an analyte based on optically detected magnetic resonance (ODMR), the system comprising: (a) a plurality of functionalized beads of a first type, which are magnetic functionalized beads and are functionalized to include a first moiety that associates with an analyte under suitable conditions, (b) a plurality of functionalized beads of a second type, which are functionalized to include a second moiety that associates with the analyte under suitable conditions, (c) a substrate including at least one ODMR center, (d) a light source configured to generate incident light that excites electrons within the at least one ODMR center from a ground state to an excited state, (e) a magnet for applying a bias magnetic field on a complex disposed over the at least one ODMR center, the complex including one of the first type of functionalized bead, the analyte, and one of the second type of functionalized bead, (f) a microwave source configured to generate a microwave field incident on the at least one ODMR center, the microwave source being further configured to generate the microwave field with frequencies that correspond to ground state transitions in the at least one ODMR center, in which the at least one ODMR center produces emitted light when illuminated by the incident light, characteristics of the emitted light being influenced by the microwave field and by the magnetic functionalized bead associated with the analyte in the complex, and an optical photodetector that detects light emitted by the at least one ODMR center.

Example 2 includes the subject matter of Example 1, wherein the at least one ODMR center is a silicon vacancy center in a silicon carbide lattice.

Example 3 includes the subject matter of Example 1, wherein the at least one ODMR center is a silicon vacancy center in a diamond lattice.

Example 4 includes the subject matter of Example 1, wherein the at least one ODMR center is a nitrogen-vacancy center in a diamond lattice.

Example 5 includes the subject matter of Example 4, wherein the at least one ODMR center is formed in an upper surface of the substrate.

Example 6 includes the subject matter of Example 5, wherein the at least one ODMR center is a plurality of ODMR centers formed in the upper surface of the diamond substrate.

Example 7 includes the subject matter of Example 6, wherein the optical photodetector is an optical imaging system having an imaging sensor that images the emitted light from the plurality of ODMR centers.

Example 8 includes the subject matter of any of Examples 1-7, wherein each of the first and the second moiety is a receptor, protein, antibody, cell, virus, or nucleic acid sequence.

Example 9 includes the subject matter of any of Examples 1-8, wherein the functionalized beads of the first type are superparamagnetic functionalized beads including a superparamagnetic material.

Example 10 includes the subject matter of Example 9, wherein the functionalized beads of the first type include a nonmagnetic layer encapsulating the superparamagnetic material.

Example 11 includes the subject matter of Example 9, wherein the superparamagnetic functionalized beads include iron oxide particles.

Example 12 includes the subject matter of any of Examples 1-11, wherein the functionalized beads of the first type comprise magnetic nanoparticles disposed within a polymer substrate.

Example 13 includes the subject matter of any of Examples 1-11, wherein the functionalized beads of the first type comprise magnetic nanoparticles disposed on a surface of a polymer substrate.

Example 14 includes the subject matter of any of Examples 1-13, wherein the functionalized beads of the second type are fluorescent functionalized beads.

Example 15 includes the subject matter of any of Examples 1-13, wherein the functionalized beads of the second type are magnetic functionalized beads including a quantity of magnetic material distinguishable from the functionalized beads of the first type.

Example 16 includes the subject matter of any of Examples 1-13, wherein the functionalized beads of the second type are magnetic functionalized beads, the second type of functionalized beads including a magnetic property distinguishable from the functionalized beads of the first type.

Example 17 includes the subject matter of Example 16, wherein the functionalized beads of the first type are superparamagnetic functionalized beads including a superparamagnetic material.

Example 18 includes the subject matter of Example 17, wherein the functionalized beads of the first type include a nonmagnetic layer encapsulating the superparamagnetic material.

Example 19 includes the subject matter of Example 16, wherein the functionalized beads of the second type are ferromagnetic functionalized beads including a ferromagnetic material.

Example 20 includes the subject matter of Example 19, wherein the functionalized beads of the second type include a nonmagnetic layer encapsulating the ferromagnetic material.

Example 21 includes the subject matter of any of Examples 1-20, wherein each of the first type of functionalized beads and the second type of functionalized beads has a diameter in a range of between 50 nm and 10 μm.

Example 22 includes the subject matter of Example 21, wherein each of the diameters of the functionalized beads of the first type and the second type is in a range of between 0.5 μm and 5 μm.

Example 23 includes the subject matter of Example 21, wherein the diameter of the functionalized beads of the first type is similar to the diameter of the functionalized beads of the second type.

Example 24 includes the subject matter of Example 21, wherein the diameter of the functionalized beads of the first type is different from the diameter of the functionalized beads of the second type by at least 50%.

Example 25 includes the subject matter of any of Examples 1-24, further including a plurality of functionalized beads of at least a third type, functionalized to include at least the second moiety that can specifically associate with at least a second analyte under appropriate conditions.

Example 26 includes the subject matter of Example 25, further including a plurality of functionalized beads of a fourth type, functionalized to include the second moiety that associates with the second analyte under suitable conditions.

Example 27 includes the subject matter of Example 25, wherein the functionalized beads of the first and/or second type further include at least one additional moiety that associates with the second analyte under suitable conditions.

Example 28 includes the subject matter of Example 27, further including a third moiety that associates with a third analyte under suitable conditions, wherein the functionalized beads of the first type are further functionalized to include the second moiety, and the functionalized beads of the second type are further functionalized to include the third moiety.

Example 29 is a method of detecting a complex including an analyte, the method comprising: (a) contacting a sample in a solution with a population of functionalized beads of a first type, which are magnetic functionalized beads and are functionalized to include a first moiety that associates with an analyte under suitable conditions, (b) contacting the sample solution with a population of functionalized beads of a second type, which are functionalized to include a second moiety that associates with the analyte under suitable conditions, contact resulting in formation of a complex including one of the first type of functionalized bead, the analyte, and one of the second type of functionalized bead; and (c) detecting the complex including the analyte by detecting magnetic fields produced by the magnetic functionalized bead and by detecting the functionalized bead of the second type associated with the analyte in the complex.

Example 30 includes the subject matter of Example 29, further including disposing the sample solution including the complex over a substrate that includes at least one optically detected magnetic resonance (ODMR) center formed in the substrate; exciting electrons within the at least one ODMR center from a ground state to an excited state with incident light; applying a bias magnetic field on the complex; and generating a microwave field incident on the at least one ODMR center, the microwave field including frequencies that correspond to ground state transitions in the at least one ODMR center, wherein detecting the complex including the analyte further includes analyzing light emitted by the at least one ODMR center, characteristics of the emitted light being influenced by the microwave field and by the magnetic functionalized bead associated with the analyte in the complex.

Example 31 includes the subject matter of Example 30, wherein the at least one ODMR center is a nitrogen-vacancy center in a diamond lattice.

Example 32 includes the subject matter of Example 31, wherein the at least one ODMR center is formed in an upper surface of the substrate.

Example 33 includes the subject matter of Example 32, wherein the at least one ODMR center is a plurality of ODMR centers formed in the upper surface of the substrate.

Example 34 includes the subject matter of Example 33, wherein analyzing light emitted by the plurality of ODMR centers includes imaging the emitted light.

Example 35 includes the subject matter of any of Examples 29-34, further including applying a magnetic field gradient to the sample solution after contacting the sample with the population of functionalized beads of the first type.

Example 36 includes the subject matter of Example 35, wherein applying the magnetic field gradient to the sample solution is performed after contacting the sample solution with the population of functionalized beads of the second type.

Example 37 includes the subject matter of any of Examples 29-36, wherein the population of functionalized beads of the first type and the population of functionalized beads of the second type are added to the sample solution sequentially.

Example 38 includes the subject matter of any of Examples 29-37, wherein the functionalized beads of the second type are fluorescent functionalized beads, and the method further includes illuminating the complex with incident light that excites fluorescence within the functionalized beads of the second type and fluorescence imaging of the complex.

Example 39 includes the subject matter of any of Examples 29-37, wherein the functionalized beads of the second type are magnetic functionalized beads, including a magnetic property distinguishable from the functionalized beads of the first type.

Example 40 includes the subject matter of any of Examples 29-39, further including applying a magnetic field gradient to the sample solution after contacting the sample solution with the functionalized beads of the first and second types.

Example 41 includes the subject matter of Example 40, further including varying the magnetic field gradient applied to the sample solution.

Example 42 includes the subject matter of any of Examples 29-41, further including concentrating the sample solution after contacting the sample solution with the population of functionalized beads of the second type.

Example 43 includes the subject matter of any of Examples 29-42, further including agglomerating a plurality of functionalized beads of the first and second types, after contacting the sample solution with the population of functionalized beads of the second type, before detecting the complex.

Example 44 includes the subject matter of any of Examples 29-43, further including dehydrating the sample solution after disposing the sample solution over the diamond substrate.

Example 45 is a bead-based assay system for detecting a complex including an analyte, the system comprising: (a) a plurality of functionalized beads of a first type, which are magnetic functionalized beads and are functionalized to include a first moiety that associates with an analyte under suitable conditions, (b) a plurality of functionalized beads of a second type, which are fluorescent functionalized beads, and are functionalized to include an unlabeled moiety that associates with the analyte under suitable conditions, (c) a light source configured to generate incident light that excites fluorescence within the functionalized beads of the second type, and (d) an optical photodetector that detects fluorescence emitted by the functionalized beads of the second type associated with the analyte in a complex including one of the first type of functionalized bead, the analyte, and one of the second type of functionalized bead.

Example 46 includes the subject matter of Example 45, wherein the fluorescent functionalized beads comprise a polymer substrate impregnated with a fluorescent material.

Example 47 includes the subject matter of Example 45, wherein the optical fluorescence detector includes a spectrophotometer.

Example 48 includes the subject matter of Example 45, wherein the optical fluorescence detector includes an optical imaging sensor that images the fluorescence emitted by the functionalized beads of the second type associated with the analyte in the complex.

Example 49 includes the subject matter of any of Examples 45-48, wherein the functionalized beads of the first type are superparamagnetic functionalized beads.

Example 50 includes the subject matter of Example 49, wherein the superparamagnetic functionalized beads include iron oxide particles.

Example 51 includes the subject matter of any of Examples 45-50, wherein the functionalized beads of the first type include magnetic nanoparticles disposed within the polymer substrate.

Example 52 includes the subject matter of any of Examples 45-50, wherein the functionalized beads of the first type include magnetic nanoparticles disposed on a surface of the polymer substrate.

Example 53 is a method of detecting a complex including an analyte, the method comprising: (a) contacting a sample in a solution with a population of functionalized beads of a first type, which are magnetic functionalized beads and are functionalized to include a first moiety that associates with an analyte under suitable conditions, (b) contacting the sample solution with a population of functionalized beads of a second type, which comprise a polymer substrate impregnated with a fluorescent material, and are functionalized to include an unlabeled moiety that associates with the analyte under suitable conditions, contact resulting in formation of a complex including one of the first type of functionalized bead, the analyte, and one of the second type of functionalized bead, (c) illuminating the complex with incident light that excites fluorescence within the functionalized beads of the second type, and (d) detecting the complex including the analyte by analyzing fluorescence emitted by the functionalized beads of the second type associated with the analyte in the complex.

Example 54 includes the subject matter of Example 53, further including applying a magnetic field gradient to the sample solution after contacting the sample with the population of functionalized beads of the first type.

Example 55 includes the subject matter of Example 54, wherein applying the magnetic field gradient to the sample solution is performed after contacting the sample solution with the population of functionalized beads of the second type.

Example 56 includes the subject matter of any of Examples 53-55, further including concentrating the sample solution after contacting the sample solution with the population of functionalized beads of the second type, before detecting the complex.

Example 57 includes the subject matter of any of Examples 53-56, further including agglomerating a plurality of functionalized beads of the first and second types, after contacting the sample solution with the population of functionalized beads of the second type, before detecting the complex.

Example 58 includes the subject matter of any of Examples 53-57, further including dehydrating the sample solution before detecting the complex.

EQUIVALENTS

Having thus described several illustrative embodiments, it is to be appreciated that various alterations, modifications, and improvements will readily occur to those skilled in the art. Such alterations, modifications, and improvements are intended to form a part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Additionally, elements and components described herein may be further divided into additional components or joined together to form fewer components for performing the same functions.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

What is claimed is:

1. A bead-based magnetic assay system for detecting a complex including an analyte based on optically detected magnetic resonance (ODMR), the system comprising:
    (a) a plurality of functionalized beads of a first type, which are magnetic functionalized beads and are functionalized to include a first moiety that associates with an analyte under suitable conditions;
    (b) a plurality of functionalized beads of a second type, which are magnetic functionalized beads including a magnetic property distinguishable from the functionalized beads of the first type and are functionalized to include a second moiety that associates with the analyte under suitable conditions;
    (c) a diamond substrate including a plurality of nitrogen-vacancy ODMR centers formed in an upper surface of the diamond substrate;
    (d) a light source configured to generate incident light that excites electrons within the at least one ODMR center from a ground state to an excited state;
    (e) a first magnet for applying a bias magnetic field on a complex disposed over the at least one ODMR center, the complex including one of the first type of functionalized bead, the analyte, and one of the second type of functionalized bead;
    (f) a microwave source configured to generate a microwave field incident on the at least one ODMR center, the microwave source being further configured to generate the microwave field with frequencies which correspond to ground state transitions in the at least one ODMR center, in which the at least one ODMR center produces emitted light when illuminated by the incident light, characteristics of the emitted light being influenced by the microwave field and by the magnetic functionalized bead associated with the analyte in the complex;
    (g) an optical imaging system having an imaging sensor that images the emitted light from the plurality of ODMR centers into spatially resolved images of the magnetic functionalized beads of the first and second type; and
    (h) a second magnet for applying a magnetizing magnetic field greater than the bias magnetic field on the complex prior to imaging the emitted light from the plurality of ODMR centers.

2. The system of claim 1, wherein the functionalized beads of the second type are ferromagnetic functionalized beads including a ferromagnetic material.

3. The system of claim 2, wherein the functionalized beads of the second type include a nonmagnetic layer encapsulating the ferromagnetic material.

4. The system of claim 1, wherein the second magnet is configured for applying the magnetizing magnetic field on the complex in a direction normal to the diamond substrate.

5. The system of claim 1, wherein the magnetizing magnetic field applied by the second magnet is greater than 200 mT.

6. The system of claim 1, wherein the functionalized beads of the first type are superparamagnetic functionalized beads including a superparamagnetic material.

7. The system of claim 6, wherein the functionalized beads of the first type include a nonmagnetic layer encapsulating the superparamagnetic material.

8. The system of claim 6, wherein the superparamagnetic functionalized beads include iron oxide particles.

9. The system of claim 1, wherein each of the first and the second moiety is a receptor, protein, antibody, cell, virus, or nucleic acid sequence.

10. The system of claim 1, wherein the functionalized beads of the first type comprise magnetic nanoparticles disposed within a polymer substrate, or on a surface of the polymer substrate.

11. The system of claim 1, wherein each of the first type of functionalized beads and the second type of functionalized beads has a diameter in a range of between 50 nm and 10 μm.

12. The system of claim 11, wherein each of the diameters of the functionalized beads of the first type and the second type is in a range of between 0.5 μm and 5 μm.

13. The system of claim 11, wherein the diameter of the functionalized beads of the first type is different from the diameter of the functionalized beads of the second type by at least 50%.

14. The system of claim 1, further including a plurality of functionalized beads of at least a third type, functionalized to include at least a third moiety that associates with at least a second analyte under suitable conditions.

15. The system of claim 14, further including a plurality of functionalized beads of a fourth type, functionalized to include at least one additional moiety that associates with the second analyte under suitable conditions.

16. The system of claim 14, wherein the functionalized beads of the first and/or second type further include at least one additional moiety that associates with the second analyte under suitable conditions.

17. The system of claim 16, further including at least one additional moiety that associates with at least a third analyte under suitable conditions, wherein the functionalized beads of the first type are further functionalized to include moieties that associate with at least the second or third analyte, and the functionalized beads of the third type are further functionalized to include moieties that associate with at least the second and third analytes.

* * * * *